US011242569B2

(12) United States Patent
Eltoukhy et al.

(10) Patent No.: US 11,242,569 B2
(45) Date of Patent: Feb. 8, 2022

(54) METHODS TO DETERMINE TUMOR GENE COPY NUMBER BY ANALYSIS OF CELL-FREE DNA

(71) Applicant: GUARDANT HEALTH, INC., Redwood City, CA (US)

(72) Inventors: Helmy Eltoukhy, Atherton, CA (US); AmirAli Talasaz, Atherton, CA (US); Darya Chudova, San Jose, CA (US); Diana Abdueva, Orinda, CA (US)

(73) Assignee: GUARDANT HEALTH, INC., Redwood City, CA (US)

( * ) Notice: Subject to any disclaimer, the term of this patent is extended or adjusted under 35 U.S.C. 154(b) by 0 days.

(21) Appl. No.: 16/737,819

(22) Filed: Jan. 8, 2020

(65) Prior Publication Data

US 2020/0140960 A1 May 7, 2020

Related U.S. Application Data

(63) Continuation of application No. 15/442,993, filed on Feb. 27, 2017, which is a continuation of application No. PCT/US2016/067356, filed on Dec. 16, 2016.

(60) Provisional application No. 62/269,051, filed on Dec. 17, 2015.

(51) Int. Cl.
*C12Q 1/6886* (2018.01)
*G16B 30/00* (2019.01)
*C12Q 1/6809* (2018.01)
*G16B 99/00* (2019.01)
*G16B 30/10* (2019.01)
*G16B 20/10* (2019.01)
*C12Q 1/6874* (2018.01)

(52) U.S. Cl.
CPC ......... *C12Q 1/6886* (2013.01); *C12Q 1/6809* (2013.01); *C12Q 1/6874* (2013.01); *G16B 20/10* (2019.02); *G16B 30/00* (2019.02); *G16B 30/10* (2019.02); *G16B 99/00* (2019.02)

(58) Field of Classification Search
None
See application file for complete search history.

(56) References Cited

U.S. PATENT DOCUMENTS

| | | | |
|---|---|---|---|
| 4,725,536 A | 2/1988 | Fritsch et al. |
| 4,942,124 A | 7/1990 | Church |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,952,170 A | 9/1999 | Stroun et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,020,124 A | 2/2000 | Sorenson |
| 6,040,138 A | 3/2000 | Lockhart et al. |
| 6,046,005 A | 4/2000 | Ju et al. |
| 6,060,596 A | 5/2000 | Lerner et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,210,891 B1 | 4/2001 | Nyren et al. |
| 6,235,475 B1 | 5/2001 | Brenner et al. |
| 6,242,186 B1 | 6/2001 | Salonen |
| 6,268,152 B1 | 7/2001 | Fodor et al. |
| 6,284,460 B1 | 9/2001 | Fodor et al. |

(Continued)

FOREIGN PATENT DOCUMENTS

CN 102933721 A 2/2013
EP 0799897 B1 6/2006

(Continued)

OTHER PUBLICATIONS

"Blood Plasma" Oxford Dictionary of Biochemistry and Molecular Biology 81 (2d ed. 2006).

(Continued)

*Primary Examiner* — Joseph Woitach
(74) *Attorney, Agent, or Firm* — Indhu Kanakaraj

(57) ABSTRACT

Methods are provided herein to improve automatic detection of copy number variation in nucleic acid samples. These methods provide improved approaches for determining baseline copy number of genetic loci within a sample, reduce variation due to features of genetic loci, sample preparation, and probe exhaustion.

18 Claims, 17 Drawing Sheets

(56) References Cited

U.S. PATENT DOCUMENTS

| | | |
|---|---|---|
| 6,300,077 B1 | 10/2001 | Shuber et al. |
| 6,306,597 B1 | 10/2001 | Macevicz |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,498,012 B2 | 12/2002 | Laken |
| 6,503,718 B2 | 1/2003 | Shuber et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,582,908 B2 | 6/2003 | Fodor et al. |
| 6,586,177 B1 | 7/2003 | Shuber |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,828,100 B1 | 12/2004 | Ronaghi |
| 6,833,246 B2 | 12/2004 | Balasubramanian |
| 6,849,403 B1 | 2/2005 | Shuber |
| 6,849,404 B2 | 2/2005 | Park et al. |
| 6,852,488 B2 | 2/2005 | Fodor et al. |
| 6,858,412 B2 | 2/2005 | Willis et al. |
| 6,964,846 B1 | 11/2005 | Shuber |
| 7,163,789 B2 | 1/2007 | Chen et al. |
| 7,208,275 B2 | 4/2007 | Gocke et al. |
| 7,232,656 B2 | 6/2007 | Balasubramanian et al. |
| 7,406,385 B2 | 7/2008 | Sorenson |
| 7,410,764 B2 | 8/2008 | Gocke et al. |
| 7,424,368 B2 | 9/2008 | Huang et al. |
| 7,424,371 B2 | 9/2008 | Kamentsky |
| 7,537,897 B2 | 5/2009 | Brenner et al. |
| 7,598,035 B2 | 10/2009 | Macevicz |
| 7,700,286 B2 | 4/2010 | Stroun et al. |
| 7,704,687 B2 | 4/2010 | Wang et al. |
| 7,727,720 B2 | 6/2010 | Dhallan |
| 7,803,929 B2 | 9/2010 | Melkonyan et al. |
| 7,811,757 B2 | 10/2010 | Shuber |
| 7,822,555 B2 | 10/2010 | Huang et al. |
| 7,824,889 B2 | 11/2010 | Vogelstein et al. |
| 7,835,871 B2 | 11/2010 | Kain et al. |
| 7,838,647 B2 | 11/2010 | Hahn et al. |
| 7,915,015 B2 | 3/2011 | Vogelstein et al. |
| 7,935,487 B2 | 5/2011 | Goeke et al. |
| 7,937,225 B2 | 5/2011 | Mishra et al. |
| 7,957,913 B2 | 6/2011 | Chinitz et al. |
| 7,960,120 B2 | 6/2011 | Rigatti et al. |
| 7,972,817 B2 | 7/2011 | Kopreski |
| 7,981,612 B2 | 7/2011 | Shuber et al. |
| 8,094,312 B2 | 1/2012 | Ulmer |
| 8,168,385 B2 | 5/2012 | Brenner |
| 8,195,415 B2 | 6/2012 | Fan et al. |
| 8,209,130 B1 | 6/2012 | Kennedy et al. |
| 8,216,789 B2 | 7/2012 | Disis et al. |
| 8,236,532 B2 | 8/2012 | Ronaghi et al. |
| 8,361,726 B2 | 1/2013 | Goeke et al. |
| 8,383,338 B2 | 2/2013 | Kitzman et al. |
| 8,383,345 B2 | 2/2013 | Shendure et al. |
| 8,455,193 B2 | 6/2013 | Travers et al. |
| 8,470,996 B2 | 6/2013 | Brenner |
| 8,481,292 B2 | 7/2013 | Casbon et al. |
| 8,603,749 B2 | 12/2013 | Gillevet |
| 8,685,678 B2 | 4/2014 | Casbon et al. |
| 8,697,408 B2 | 4/2014 | Kucera et al. |
| 8,704,165 B2 | 4/2014 | Huang |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,775,092 B2 | 7/2014 | Colwell et al. |
| 8,835,358 B2 | 9/2014 | Fodor et al. |
| 8,865,410 B2 | 10/2014 | Shendure et al. |
| 9,018,365 B2 | 4/2015 | Brenner |
| 9,085,798 B2 | 7/2015 | Chee |
| 9,121,069 B2 | 9/2015 | Lo et al. |
| 9,260,753 B2 | 2/2016 | Xie et al. |
| 9,340,830 B2 | 5/2016 | Lipson et al. |
| 9,376,719 B2 | 6/2016 | Eijk et al. |
| 9,404,156 B2 | 8/2016 | Hicks et al. |
| 9,476,095 B2 | 10/2016 | Vogelstein et al. |
| 9,598,731 B2 | 3/2017 | Talasaz |
| 9,752,188 B2 | 9/2017 | Schmitt et al. |
| 9,834,822 B2 | 12/2017 | Talasaz |
| 9,840,743 B2 | 12/2017 | Talasaz |
| 9,920,366 B2 | 3/2018 | Eltoukhy et al. |
| 10,287,631 B2 | 5/2019 | Salk et al. |
| 10,370,713 B2 | 8/2019 | Salk et al. |
| 10,385,393 B2 | 8/2019 | Salk et al. |
| 10,619,214 B2 | 4/2020 | Lo et al. |
| 2001/0053519 A1 | 12/2001 | Fodor et al. |
| 2002/0072058 A1 | 6/2002 | Voelker et al. |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0152490 A1 | 8/2003 | Trulson et al. |
| 2003/0165978 A1 | 9/2003 | Firth et al. |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0209299 A1 | 10/2004 | Pinter et al. |
| 2004/0259118 A1 | 12/2004 | Macevicz |
| 2005/0164241 A1 | 7/2005 | Hahn et al. |
| 2005/0221314 A1 | 10/2005 | Berlin et al. |
| 2005/0250147 A1 | 11/2005 | Macevicz |
| 2006/0024681 A1 | 2/2006 | Smith et al. |
| 2006/0035258 A1 | 2/2006 | Tadakamalla et al. |
| 2006/0046258 A1 | 3/2006 | Lapidus et al. |
| 2006/0073506 A1 | 4/2006 | Christians et al. |
| 2006/0211030 A1 | 9/2006 | Brenner |
| 2006/0292611 A1 | 12/2006 | Berka et al. |
| 2007/0020640 A1 | 1/2007 | McCloskey et al. |
| 2007/0065823 A1 | 3/2007 | Dressman et al. |
| 2007/0111233 A1 | 5/2007 | Bianchi et al. |
| 2007/0114362 A1 | 5/2007 | Feng et al. |
| 2007/0128724 A1 | 6/2007 | Miles et al. |
| 2007/0172839 A1 | 7/2007 | Smith et al. |
| 2007/0172873 A1 | 7/2007 | Brenner et al. |
| 2008/0014146 A1 | 1/2008 | Hoff et al. |
| 2008/0124721 A1 | 5/2008 | Fuchs et al. |
| 2008/0161420 A1 | 7/2008 | Shuber |
| 2008/0261204 A1 | 10/2008 | Lexow |
| 2008/0293055 A1 | 11/2008 | Freeman et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0105959 A1 | 4/2009 | Braverman et al. |
| 2009/0162836 A1 | 6/2009 | Widschwendter |
| 2009/0298075 A1 | 12/2009 | Travers et al. |
| 2009/0298709 A1 | 12/2009 | Ma |
| 2009/0317818 A1 | 12/2009 | Ehrich et al. |
| 2010/0041048 A1 | 2/2010 | Diehl et al. |
| 2010/0062494 A1 | 3/2010 | Church et al. |
| 2010/0069250 A1 | 3/2010 | White et al. |
| 2010/0112575 A1 | 5/2010 | Fan et al. |
| 2010/0143932 A1 | 6/2010 | Lapidus |
| 2010/0166744 A1 | 7/2010 | Wong |
| 2010/0196898 A1 | 8/2010 | Sugarbaker et al. |
| 2010/0264331 A1 | 10/2010 | Saeko et al. |
| 2010/0300559 A1 | 12/2010 | Schultz et al. |

(56) References Cited

U.S. PATENT DOCUMENTS

| | | |
|---|---|---|
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0009278 A1 | 1/2011 | Kain et al. |
| 2011/0014607 A1 | 1/2011 | Jirtle et al. |
| 2011/0160078 A1 | 6/2011 | Fodor et al. |
| 2011/0160290 A1 | 6/2011 | Tewari |
| 2011/0171640 A1 | 7/2011 | Bhatt et al. |
| 2011/0177512 A1 | 7/2011 | Shuber |
| 2011/0183330 A1 | 7/2011 | Lo et al. |
| 2011/0201507 A1 | 8/2011 | Rava et al. |
| 2011/0230358 A1 | 9/2011 | Rava |
| 2011/0230360 A1 | 9/2011 | Stephan et al. |
| 2011/0245482 A1 | 10/2011 | Hahn et al. |
| 2011/0264376 A1 | 10/2011 | Chinitz et al. |
| 2011/0275084 A1 | 11/2011 | Byron et al. |
| 2011/0281736 A1 | 11/2011 | Drmanac et al. |
| 2011/0319272 A1 | 12/2011 | Fan et al. |
| 2012/0003637 A1 | 1/2012 | Lo et al. |
| 2012/0034685 A1 | 2/2012 | Sparks et al. |
| 2012/0046877 A1 | 2/2012 | Hyland et al. |
| 2012/0053073 A1 | 3/2012 | Kassis |
| 2012/0059594 A1 | 3/2012 | Hatchwell et al. |
| 2012/0065081 A1 | 3/2012 | Chee |
| 2012/0095697 A1 | 4/2012 | Halpern et al. |
| 2012/0100548 A1 | 4/2012 | Rava et al. |
| 2012/0164630 A1 | 6/2012 | Porreca et al. |
| 2012/0165202 A1 | 6/2012 | Porreca et al. |
| 2012/0191367 A1 | 7/2012 | Stuelpnagel et al. |
| 2012/0208706 A1 | 8/2012 | Downing et al. |
| 2012/0214163 A1 | 8/2012 | Sugarbaker et al. |
| 2012/0214678 A1 | 8/2012 | Rava et al. |
| 2012/0220478 A1 | 8/2012 | Shaffer |
| 2012/0231479 A1 | 9/2012 | Puskas et al. |
| 2012/0238464 A1 | 9/2012 | Koi et al. |
| 2012/0270212 A1 | 10/2012 | Rabinowitz et al. |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0017958 A1 | 1/2013 | Benz et al. |
| 2013/0022977 A1 | 1/2013 | Lapidus et al. |
| 2013/0029852 A1 | 1/2013 | Rava et al. |
| 2013/0034546 A1 | 2/2013 | Rava et al. |
| 2013/0040824 A1 | 2/2013 | Lo et al. |
| 2013/0053256 A1 | 2/2013 | Hubbell |
| 2013/0060483 A1 | 3/2013 | Struble et al. |
| 2013/0078626 A1 | 3/2013 | Wasserstrom et al. |
| 2013/0085681 A1 | 4/2013 | Deciu et al. |
| 2013/0102485 A1 | 4/2013 | Lee |
| 2013/0102487 A1 | 4/2013 | Cos et al. |
| 2013/0116127 A1 | 5/2013 | Schuetz et al. |
| 2013/0116130 A1 | 5/2013 | Fu et al. |
| 2013/0122499 A1 | 5/2013 | Morris et al. |
| 2013/0130923 A1 | 5/2013 | Ehrich et al. |
| 2013/0137588 A1 | 5/2013 | Shendure et al. |
| 2013/0143747 A1 | 6/2013 | Gutin et al. |
| 2013/0210643 A1 | 8/2013 | Casbon et al. |
| 2013/0210645 A1 | 8/2013 | Volgelstein et al. |
| 2013/0224743 A1 | 8/2013 | Casbon et al. |
| 2013/0237431 A1 | 9/2013 | Lo et al. |
| 2013/0237458 A1 | 9/2013 | Casbon et al. |
| 2013/0260381 A1 | 10/2013 | Ramakrishnan |
| 2013/0267424 A1 | 10/2013 | Casbon et al. |
| 2013/0338933 A1 | 12/2013 | Deciu et al. |
| 2014/0011694 A1 | 1/2014 | Couronne |
| 2014/0065609 A1 | 3/2014 | Hicks et al. |
| 2014/0065630 A1 | 3/2014 | Bubnoff et al. |
| 2014/0066317 A1 | 3/2014 | Talasaz |
| 2014/0100121 A1 | 4/2014 | Lo et al. |
| 2014/0242588 A1 | 8/2014 | Boom et al. |
| 2014/0274731 A1 | 9/2014 | Raymond et al. |
| 2014/0274740 A1 | 9/2014 | Srinivasan et al. |
| 2014/0296094 A1 | 10/2014 | Domanus |
| 2014/0303008 A1 | 10/2014 | Schutz et al. |
| 2014/0336943 A1 | 11/2014 | Pellini et al. |
| 2014/0350130 A1 | 11/2014 | Sanborn et al. |
| 2014/0357500 A1 | 12/2014 | Vigneault et al. |
| 2015/0004158 A1 | 1/2015 | Shipp et al. |
| 2015/0024950 A1 | 1/2015 | Bielas et al. |
| 2015/0044687 A1 | 2/2015 | Schmitt et al. |
| 2015/0050647 A1 | 2/2015 | Luo et al. |
| 2015/0051085 A1 | 2/2015 | Vogelstein et al. |
| 2015/0065358 A1 | 3/2015 | Comstock et al. |
| 2015/0080266 A1 | 3/2015 | Volkmuth et al. |
| 2015/0087535 A1 | 3/2015 | Patel |
| 2015/0167069 A1 | 6/2015 | Schutz et al. |
| 2015/0197786 A1 | 7/2015 | Osborne et al. |
| 2015/0275289 A1 | 10/2015 | Otwinowski et al. |
| 2015/0299812 A1 | 10/2015 | Talasaz |
| 2015/0329917 A1 | 11/2015 | Shuber |
| 2015/0344970 A1 | 12/2015 | Vogelstein et al. |
| 2015/0366866 A1 | 12/2015 | Ali et al. |
| 2015/0368708 A1 | 12/2015 | Talasaz |
| 2016/0002739 A1 | 1/2016 | Schutz et al. |
| 2016/0002741 A1 | 1/2016 | Kitano et al. |
| 2016/0024576 A1 | 1/2016 | Chee |
| 2016/0026758 A1 | 1/2016 | Jabara et al. |
| 2016/0032396 A1 | 2/2016 | Diehn et al. |
| 2016/0040229 A1 | 2/2016 | Talasaz et al. |
| 2016/0046986 A1 | 2/2016 | Eltoukhy et al. |
| 2016/0053301 A1 | 2/2016 | Raymond et al. |
| 2016/0060691 A1 | 3/2016 | Giresi et al. |
| 2016/0071432 A1 | 3/2016 | Kurowski et al. |
| 2016/0115553 A1 | 4/2016 | Stephan et al. |
| 2016/0130649 A1 | 5/2016 | Xie et al. |
| 2016/0251704 A1 | 9/2016 | Talasaz et al. |
| 2016/0319345 A1 | 11/2016 | Gnerre et al. |
| 2016/0333417 A1 | 11/2016 | Talasaz |
| 2016/0376647 A1 | 12/2016 | Travers et al. |
| 2017/0051347 A1 | 2/2017 | Vogelstein et al. |
| 2017/0073774 A1 | 3/2017 | Lo et al. |
| 2017/0145516 A1 | 5/2017 | Kopetz et al. |
| 2017/0159120 A1 | 6/2017 | Eijk et al. |
| 2017/0211143 A1 | 7/2017 | Shendure et al. |
| 2017/0218459 A1 | 8/2017 | Talasaz et al. |
| 2017/0218460 A1 | 8/2017 | Talasaz |
| 2017/0233829 A1 | 8/2017 | Lo et al. |
| 2018/0023125 A1 | 1/2018 | Talasaz et al. |
| 2018/0251848 A1 | 9/2018 | Diehn et al. |
| 2019/0292607 A1 | 9/2019 | Lo et al. |
| 2020/0056242 A1 | 2/2020 | Lo et al. |

FOREIGN PATENT DOCUMENTS

| | | |
|---|---|---|
| EP | 1647600 A2 | 6/2006 |
| EP | 2110442 A1 | 10/2009 |
| EP | 3070177 A1 | 9/2016 |
| EP | 3178941 A1 | 6/2017 |
| EP | 3230469 B1 | 4/2019 |
| EP | 2527471 B1 | 3/2020 |
| WO | 1997007241 A1 | 2/1997 |
| WO | 1997010365 A1 | 3/1997 |
| WO | 1999028505 A1 | 6/1999 |
| WO | 2000058516 A2 | 10/2000 |
| WO | 2002056014 A2 | 7/2002 |
| WO | 2005080604 A2 | 9/2005 |
| WO | 2005111242 A2 | 11/2005 |
| WO | 2006102264 A1 | 9/2006 |
| WO | 2007037678 A2 | 4/2007 |
| WO | 2008070144 A2 | 6/2008 |
| WO | 2008154317 A1 | 12/2008 |
| WO | 2009152928 A2 | 12/2009 |
| WO | 2011060240 A1 | 5/2011 |
| WO | 2011087760 A2 | 7/2011 |
| WO | 2011091046 A1 | 7/2011 |
| WO | 2011103236 A2 | 8/2011 |
| WO | 2011140510 A2 | 11/2011 |
| WO | 2011155833 A2 | 12/2011 |
| WO | 2012012693 A2 | 1/2012 |
| WO | 2012014877 A1 | 2/2012 |
| WO | 2012019200 A2 | 2/2012 |
| WO | 2012028746 A1 | 3/2012 |

(56) References Cited

FOREIGN PATENT DOCUMENTS

| | | | |
|---|---|---|---|
| WO | 2012038839 A2 | 3/2012 |
| WO | 2012042374 A2 | 4/2012 |
| WO | 2012048341 A1 | 4/2012 |
| WO | 2012054873 A2 | 4/2012 |
| WO | 2012066451 A1 | 5/2012 |
| WO | 2012071621 A1 | 6/2012 |
| WO | 2012088348 A2 | 6/2012 |
| WO | 2012106559 A1 | 8/2012 |
| WO | 2012129363 A2 | 9/2012 |
| WO | 2012142213 A2 | 10/2012 |
| WO | 2012142611 A2 | 10/2012 |
| WO | 2012103031 A3 | 1/2013 |
| WO | 2013019075 A2 | 2/2013 |
| WO | 2013033721 A1 | 3/2013 |
| WO | 2013106737 A1 | 7/2013 |
| WO | 2013123442 A1 | 8/2013 |
| WO | 2013130512 A2 | 9/2013 |
| WO | 2013130674 A1 | 9/2013 |
| WO | 2013138510 A1 | 9/2013 |
| WO | 2013142213 A1 | 9/2013 |
| WO | 2013142389 A1 | 9/2013 |
| WO | 2013148496 A1 | 10/2013 |
| WO | 2013159035 A2 | 10/2013 |
| WO | 2013166517 A1 | 11/2013 |
| WO | 2013173394 A2 | 11/2013 |
| WO | 2013181170 A1 | 12/2013 |
| WO | 2013188471 A2 | 12/2013 |
| WO | 2013190441 A2 | 12/2013 |
| WO | 2014004726 A1 | 1/2014 |
| WO | 2014014497 A1 | 1/2014 |
| WO | 2014015319 A1 | 1/2014 |
| WO | 2014039556 A1 | 3/2014 |
| WO | 2014093330 A1 | 6/2014 |
| WO | 2014145078 A1 | 9/2014 |
| WO | 2014149134 A2 | 9/2014 |
| WO | 2014151117 A1 | 9/2014 |
| WO | 2014152990 A1 | 9/2014 |
| WO | 2014165596 A1 | 10/2014 |
| WO | 2015100427 A1 | 7/2015 |
| WO | 2015159293 A2 | 10/2015 |
| WO | 2015184404 A1 | 12/2015 |
| WO | 2016015058 A2 | 1/2016 |
| WO | 2016040901 A1 | 3/2016 |
| WO | 2016109452 A1 | 7/2016 |
| WO | 2017100441 A1 | 6/2017 |
| WO | 2017181146 A1 | 10/2017 |

OTHER PUBLICATIONS

"LB-246/12—Detection of circulating tumor DNA in early stage cancers," Available at https://www.genomeweb.com/cancer/ngs-error-correction-method-described-aacr-excitement-grows-early-cancer-detection, Accessed on Apr. 26, 2017.
"Cohesive End," Oxford Dictionary of Biochemistry and Molecular Biology 132 (2d ed. 2006).
"Control," Oxford Dictionary of Biochemistry and Molecular Biology (2d ed. 2006), 143.
Ajay, S.S. et al., "Accurate and comprehensive sequencing of personal genomes," Genome Res. 2011, 21(9), 1498-1505.
Albert, T.J. et al., "Direct selection of human genomic loci by microarray hybridization," Nat. Methods 2007, 4(11), 903-905.
Alkan, et al. Personalized copy number and segmental duplication maps using next-generation sequencing. Nat Genet. Oct. 2009;41(10):1061-7. doi: 10.1038/ng.437. Epub Aug. 30, 2009.
Andersson, et al. Bayesian detection of periodic mRNA time profiles without use of training examples. BMC Bioinformatics. Feb. 9, 2006;7:63.
Angeloni, D. Molecular analysis of deletions in human chromosome 3p21 and the role of resident cancer genes in disease. Brief Funct Genomic Proteomic Mar. 2007;6(1):19-39 Epub May 24, 2007.
Ansorge "Next-generation DNA sequencing techniques." New Biotechnology, 25(4):195-203 (2009).
Appel, Maryke. Part II: It's all about conversion. Kapa Biosystems. Accessed Mar. 29, 2017. Printed Apr. 11, 2017. 5 pages. URL:https://www.kapabiosystems.com/ngs/part-ii-conversion/.
Arneson, N. et al., "Whole-Genome Amplification by Adaptor-Ligation PCR of Randomly Sheared Genomic DNA (PRSG)," CSH Protocols, 2008, 3(1).
Ashford, Monica. NGS Error Correction Method Described at AACR as Excitement Grows for Early Cancer Detection. Genomeweb.com. Apr. 5, 2017. 3 pages. URL:https://www.genomeweb.com/cancer/ngs-error-correction-method-described-aacr-excitement-grows-early-cancer-detection.
Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.
Audic, et al. "The Significance of Digital Gene Expression Profiles." Genome Research, 7: 986-995 (1997).
Barzon, et al. Evaluation of circulating thyroid-specific transcripts as markers of thyroid cancer relapse. Int J Cancer. Jul. 20, 2004;110(6):914-20.
Bendich, et al. Circulating DNA as a possible factor in oncogenesis. Science. Apr. 16, 1965;148(3668):374-6.
Bentley, D.R. et al., "Accurate Whole Human Genome Sequencing using Reversible Terminator Chemistry," Nature, 2008, 456(7218):53-59.
Bettegowda et al., "Detection of Circulating Tumor DNA in Early- and Late-Stage Human Malignancies," Sci. Transl. Med. 2014, 6(224):224ra24.
Bianchi, D.W. et al. "Genome-Wide Fetal Aneuploidy Detection by Maternal Plasma DNA Sequencing," Obstetrics & Gynecology, (2012) 119(5), 1-12.
Bonaldo, et al. Normalization and subtraction: two approaches to facilitate gene discovery. Genome Res. Sep. 1996;6(9):791-806.
Bowcock, et al. Exclusion of the retinoblastoma gene and chromosome 13q as the site of a primary lesion for human breast cancer. Am J Hum Genet. Jan. 1990;46(1):12-7.
Braha, et al. Simultaneous stochastic sensing of divalent metal ions. Nature Biotechnology, 18: 1005-1007 (2000).
Bremnes, et al. Circulating tumour-derived DNA and RNA markers in blood: a tool for early detection, diagnostics, and follow-up? Lung Cancer. Jul. 2005;49(1):1-12.
Brenner, et al. "Gene expression analysis by massively parallel signature sequencing (MPSS) on microbead arrays." Nature Biotechnology, 18: 630-634 (2000).
Brenner, et al. In vitro cloning of complex mixtures of DNA on microbeads: physical separation of differentially expressed cDNAs. Proc Natl Acad Sci USA. Feb. 15, 2000;97(4):1665-70.
Bryzgunova,O. et al., "A reliable method to concentrate circulating DNA," Analytical Biochem., 2010, 408:354-356.
Campbell, et al. Identification of somatically acquired rearrangements in cancer using genome-wide massively parallel paired-end sequencing. Nat Genet. Jun. 2008;40(6):722-9. doi: 10.1038/ng.128. Epub Apr. 27, 2008.
Caramazza, et al. Chromosome 1 abnormalities in myeloid malignancies: a literature survey and karyotype-phenotype associations. Eur J Haematol. Mar. 2010;84(3):191-200. doi: 10.1111/j.1600-0609.2009.01392.x. Epub Nov. 30, 2009.
Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.
Casava v1.8.2 User Guide http://gensoft.pasteur.fr/docs/casava/1.8.2/CASAVA_1_8_2_UG_15011196C.pdf (Oct. 2011).
Casbon, et al. A method for counting PCR template molecules with application to next-generation sequencing. Nucleic Acids Res. Jul. 2011;39(12):e81. doi: 10.1093/nar/gkr217. Epub Apr. 13, 2011.
Castle, et al. DNA copy number including telomeres and mitochondria, assayed using next-generation sequencing. BMC Genomics. Apr. 16, 2010;11:244. doi: 10 1186/1471-2164-11-244.
Chang, et al. Detection of allelic imbalance in ascitic supernatant by digital single nucleotide polymorphism analysis. Clin Cancer Res. Aug. 2002;8(8):2580-5.

(56) References Cited

OTHER PUBLICATIONS

Chee, et al. "Accessing genetic information with high-density DNA arrays." Science, 274: 610-614 (1996).
Chee. "Enzymatic multiplex DNA sequencing." Nucleic Acids Research, 19(12): 3301-3305 (1991).
Chen, et al. Microsatellite alterations in plasma DNA of small cell lung cancer patients. Nat Med. Sep. 1996;2(9):1033-5.
Chin, et al. A SNP in a let-7 microRNA complementary site in the KRAS 3' untranslated region increases non-small cell lung cancer risk Cancer Res. Oct. 15, 2008;68(20):8535-40. doi: 10.1158/0008-5472.CAN-08-2129.
Chiu, et al. Non-invasive prenatal assessment of trisomy 21 by multiplexed maternal plasma DNA sequencing: large scale validity study BMJ. Jan. 11, 2011;342:c7401. doi: 10 1136/bmj.c7401.
Chiu, et al. Quantitative analysis of circulating mitochondrial DNA in plasma. Clin Chem. May 2003;49(5):719-26.
Chiu, R.W.K. et al. "Noninvasive prenatal diagnosis of fetal chromosomal aneuploidy by massively parallel genomic sequencing of DNA in maternal plasma" PNAS (2008) 105(51):20458-20463.
Church, et al. "Multiplex DNA sequencing." Science, 240: 185-188 (1988).
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
Cook, et al. Methylated DNA labels for marking objects. Biotechnol Lett. Jan. 2003;25(1):89-94.
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.
Coulet, et al. Detection of plasma tumor DNA in head and neck squamous cell carcinoma by microsatellite typing and p53 mutation analysis. Cancer Res. Feb. 1, 2000;60(3):707-11.
Cox, J. "Bar coding objects with DNA." Analyst. May 2001;126(5):545-7.
Craig, et al. Identification of genetic variants using bar-coded multiplexed sequencing. Nat Methods. Oct. 2008;5(10):887-93. doi: 10.1038/nmeth.1251. Epub Sep. 14, 2008.
Daines, et al. High-throughput multiplex sequencing to discover copy number variants in *Drosophila*. Genetics. Aug. 2009;182(4):935-41. doi: 10 1534/genetics.109.103218. Epub Jun. 15, 2009.
D'Antoni, et al. Rapid quantitative analysis using a single molecule counting approach. Anal Biochem. May 1, 2006;352(1):97-109. Epub Feb. 10, 2006.
Pleasance, et al. A small-cell lung cancer genome with complex signatures of tobacco exposure. Nature. Jan. 14, 2010;463(7278):184-90. doi: 10.1038/nature08629. Epub Dec. 16, 2009.
Pollack, et al. Genome-wide analysis of DNA copy-number changes using cDNA microarrays. Nat Genet. Sep. 1999;23(1):41-6.
Pozhitkov, A.E. et al., A Revised Design for Microarray Experiments to Account for Experimental Noise and Uncertainty of Probe Response. PLoS One. 2014, vol. 9, No. 3, p. e91295 (10 pages).
Qiu, et al. DNA sequence-based "bar codes" for tracking the origins of expressed sequence tags from a maize cDNA library constructed using multiple mRNA sources Plant Physiol. Oct. 2003;133(2):475-81.
Quail, et al. A large genome center's improvements to the Illumina sequencing system. Nat Methods. Dec. 2008;5(12):1005-10. doi: 10.1038/nmeth.1270.
Quinlan, A.R. et al., "Pyrobayes: an improved base caller for SNP discovery in pyrosequences," Nat. Methods 2008 5(2), 179-181.
Rafi, I. et al. "Cell-free fetal DNA and non-invasive prenatal diagnosis," Br. J. Gen. Pract. May 1, 2009; 59(562)e146-3148.
Rand, et al. Headloop suppression PCR and its application to selective amplification of methylated DNA sequences. Nucleic Acids Res. Aug. 9, 2005;33(14):e127.
Redon, R. et al., "Global variation in copy number in the human genome," Nature 2006 444(7118), 444-454.
Rizzo, J.M. et al. "Key Principles and Clinical Applications of 'Next Generation' DNA Sequencing," Cancer Prev. Res., (2012) 5, 887-900.
Rothberg, et al., An integrated semiconductor device enabling non-optical genome sequencing, Nature, 2011, 475:348-52.
Ryan, et al. A prospective study of circulating mutant KRAS2 in the serum of patients with colorectal neoplasia: strong prognostic indicator in postoperative follow up. Gut. Jan. 2003;52(1):101-8.
Rygaard, et al. Abnormalities in structure and expression of the retinoblastoma gene in small cell lung cancer cell lines and xenografts in nude mice. Cancer Res. Sep. 1, 1990;50(17):5312-7.
Sanger, F. et al. "DNA sequencing with chain-terminating inhibitors" PNAS (1977) 74(12):5463-5467.
Sausen, M. et al. "Integrated genomic analyses identify ARID1A and ARID1B alterations in the childhood cancer neuroblastoma", Nature Genetics 2013, 45(1), 12-17.
Schmitt et al. Supplemental Information http://www.pnas.org/content/suppl/2012/08/01/1208715109. DCSupplemental.
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Schwarzenbach, et al. A critical evaluation of loss of heterozygosity detected in tumor tissues, blood serum and bone marrow plasma from patients with breast cancer. Breast Cancer Res. 2007;9(5):R66.
Schwarzenbach, et al. Cell-free tumor DNA in blood plasma as a marker for circulating tumor cells in prostate cancer. Clin Cancer Res. Feb. 1, 2009;15(3):1032-8. doi: 10.1158/1078-0432.CCR-08-1910.
Schwarzenback, H. et al. "Cell-free nucleic acids as biomarkers in cancer patients" Nature Reviews Cancer (2011) 11:426-437.
Schweiger et al., "Genome-wide massively parallel sequencing of formaldehyde fixed-paraffin embedded (FFPE) tumor tissues for copy-number- and mutation-analysis," PLoS One 2009, 4(5), e5548.
Sebat, et al. Large-Scale Copy Number Polymorphism in the Human Genome. Science, 305: 525-528 (2004).
Sehnert, A.J. et al. "Optimal Detection of Fetal Chromosomal Abnormalities by Massively Parallel DNA Sequencing of Cell-Free Fetal DNA from Maternal Blood" Clin Chem (2011) 57(7):1042-1049.
Shaw et al. Genomic analysis of circulating cell-free DNA infers breast cancer dormancy. Genome Research 22(2):220-231 (Feb. 2012).
Shaw, et al. Microsatellite alterations plasma DNA of primary breast cancer patients. Clin Cancer Res. Mar. 2000;6(3):1119-24.
Shendure, J. et al. "Next-generation DNA sequencing," Nat. Biotechnol. 2008 26(10), 1135-1145.
Shinozaki, et al. Utility of circulating B-RAF DNA mutation in serum for monitoring melanoma patients receiving biochemotherapy. Clin Cancer Res. Apr. 1, 2007;13(7):2068-74.
Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/pnas.1118018109. Epub Jan. 9, 2012.
Shoemaker, et al. Quantitative phenotypic analysis of yeast deletion mutants using a highly parallel molecular bar-coding strategy. Nature Genetics, 14: 450-456 (1996).
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Smith, et al. Highly-multiplexed barcode sequencing: an efficient method for parallel analysis of pooled samples. Nucleic Acids Research, 38(13): e142 (2010).
Smith, T.F. et al. "Comparison of Biosequences" Adv App Math (1981) 2:482-489.
Sorenson, et al. Soluble normal and mutated DNA sequences from single-copy genes in human blood. Cancer Epidemiol Biomarkers Prev. Jan.-Feb. 1994;3(1):67-71.
Sparks, et al. Selective analysis of cell-free DNA in maternal blood for evaluation of fetal trisomy. Prenat Diagn. Jan. 2012;32(1):3-9. doi: 10.1002/pd.2922. Epub Jan. 6, 2012.
Stein, et al. "The case for cloud computing in genome informatics", Genome Biol. 2010; 11 (5):207. Epub May 5, 2010.

(56) References Cited

OTHER PUBLICATIONS

Steinman. Free DNA in serum and plasma from normal adults. J Clin Invest. Aug. 1975;56(2):512-5.
Stitziel, et al. Computational and statistical approaches to analyzing variants identified byexome sequencing. Genome Biol. Sep. 14, 2011;12(9):227. doi: 10.1186/GB-2011-12-9-227.
Stroun, M, et al., "About the possible orgin and mechanism of circulating DNA apoptosis and active DNA release", Clin Shim Acta, vol. 313, No. 1-2, pp. 139-142, (2001).
Stumm, M. et al. "Noninvasive prenatal detection of chromosomal aneuploidies using different next generation sequencing stralegies and algorithms" Prenatal Diagnosis (2012) 32:569-577.
Taback, et al. Detection of tumor-specific genetic alterations in bone marrow from early-stage breast cancer patients. Cancer Res. Apr. 15, 2003;63(8):1884-7.
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.
Teer, J.K. et al. "Systematic comparison of three genomic enrichment methods for massively parallel DNA sequencing" Genome Res (2010) 20(10):1420-1431.
Tie, J. et al., "Circulating tumor DNA analysis detects minimal residual disease and predicts recurrence in patients with stage II colon cancer,"Sci. Transl. Med. 2016, 8(346):346ra92.
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
Tomlinson, et al. A genome-wide association scan of tag SNPs identifies a susceptibility variant for colorectal cancer at 8q24.21. Nat Genet. Aug. 2007;39(8):984-8. Epub Jul. 8, 2007.
Tsai, et al. Discovery of rare mutations in populations: Tilling by sequencing. Plant Physiol. Jul. 2011; 156(3):1257-68. doi: 10.1104/pp.110.169748. Epub Apr. 29, 2011.
U.S. Appl. No. 61/613,413 ("Schmitt '413 provisional"), filed Mar. 20, 2012.
U.S. Appl. No. 61/625,319 ("Schmitt '319 provisional"), filed Apr. 17, 2012.
UCSC Genome Bioinformatics. About the UCSC Genome Bioinformatics Site, http://genome.ucsc.edu/index.html. Accessed on May 26, 2015. 2 pgs.
Extended European search report and opinion dated Mar. 3, 2020 for EP Application No. 16876854.7.
Japanese Office action dated Oct. 5, 2020 for JP2018-531350.
Singapore written opinion dated Jan. 5, 2021 for 11201805119Q.
Singapore written opinion dated Jan. 17, 2020 for 11201805119Q.
Hyland, et al. The normal and tumor spectrum of copy number variation: Copy number alterations correlate with changes in gene expression in tumor transcriptome. Nov. 15, 2009. 1 page. Retreived from:http://tools.thermofisher.com/content/sfs/posters/cms_073633.pdf.
Iafrate, et al. Detection of large-scale variation in the human genome. Nat Genet. Sep. 2004;36(9):949-51. Epub Aug. 1, 2004.
Ikeguchi, et al. Detection of loss of heterozygosityat microsatellite loci in esophageal squamous-cell carcinoma. Oncology. 1999;56(2):164-8.
Illumina "Multiplexed Sequencing with Illumina Genome Analyzer System" https://www.illumina.com/Documents/products/datasheets/datasheet_sequencing_multiplex.pdf (Dec. 2008).
Illumina Preparing Samples for Paired-End Sequencing (2008).
Ingolia, et al. Genome-wide analysis in vivo of translation with nucleotide resolution using ribosome profiling. Science Apr. 10, 2009;324(5924):218-23. Epub Feb. 12, 2009.
Instructions for Norit Rapid DNA Ligation Kit (Nov. 6, 2004).
International search report and written opinion dated Mar. 9, 2017 for PCT/US2016/067356.
Invitrogen Instructions for T4 DNA Ligase (May 5, 2002).
Jabara, C. Capturing the cloud: High throughput sequencing of multiple individual genomes from a retroviral population. Biology Lunch Bunch Series, Training Initiatives in Biomedical & Biological Sciences of the University of Horth Carolina at Chapel Hill, Apr. 23, 2010.
Jabara, et al. Accurate sampling and deep sequencing of the HIV-1 protease gene using a Primer ID. (Paper # 665), The 18th Annual Conference on Retroviruses and Opportunistic Infections, Boston, Massachusetts, Mar. 2011.
Jabara, et al. Accurate sampling and deep sequencing of the HIV-1 protease gene using a Primer ID. Proc Natl Acad Sci U S A. Dec. 13, 2011;108(50):20166-71. doi: 10.1073/pnas.1110064108. Epub Nov. 30, 2011.
Jahr, et al. DNA fragments in the blood plasma of cancer patients: quantitations and evidence for their origin from apoptotic and necrotic cells. Cancer Res. Feb. 15, 2001;61(4):1659-65.
Jeronimo, et al. Quantitative GSTP1 hypermethylation in bodily fluids of patients with prostate cancer. Urology. Dec. 2002;60(6):1131-5.
Jiang, H. et al., "SeqMap: mapping massive amount of oligonucleotides to the genome," Bioinformatics 2008, 24(20):2395-2396.
Kanagawa. Bias and artifacts in multitemplate polymerase chain reactions (PCR), 2003, Journal of Bioscience and Bioengineering, vol. 96, No. 4, p. 317-323.
Kao,W-C. et al., "BayesCall: A model-based base-calling algorithm for high-throughput short-read sequencing," Genome Res 2009 19(10), 1884-1895.
Karow, J. "Hopkins Team Develops Method to Improve Rare Mutation Detection for Early Cancer Dx" Genome Web (2011) 3 pages.
Kennedy, S.R. et al., "Detecting ultralow-frequency mutations by Duplex Sequencing," Nat. Protoc. 2014, 9(11), 2586-2606.
Kim, S.Y. et al. "Estimation of allele frequency and association mapping using next-generation sequencing data" BMC Bioinformatics (2011) 12:231 (16 pages).
Kimura, et al. EGFR mutation status in tumour-derived DNA from pleural effusion fluid is a practical basis for predicting the response to gefitinib. Br J Cancer. Nov. 20, 2006;95(10):1390-5. Epub Oct. 24, 2006.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kinde, et al. Supplemental Information, Detection and quantification of rare mutations with massively parallel sequencing. Proc Natl Acad Sci USA. Jun. 7, 2011;108(23):1-10.
Kinde, I. et al., "Evaluation of DNA from the Papanicolaou Test to Detect Ovarian and Endometrial Cancers," Sci. Transl. Med. 2013, 5(167):167ra4.
Kinde, I. et al., "FAST-SeqS: a simple and efficient method for the detection of aneuploidy by massively parallel sequencing," PLoS One 2012, 7(7), e41162.
Kircher, M. et al., "Improved base calling for the Illumina Genome Analyzer using machine learning strategies," Genome Biol. 2009, 10(8), R83.
Kirsch, S. et al. "Sequence error storms and the landscape of mutations in cancer," Proc. Natl. Acad. Sci. USA 2012, 109(36), 14289-14290.
Kivioja, T., et al. Counting absolute numbers of molecules using unique molecular identifiers. Nat Methods. Nov. 20, 2011;9(1):72-4 doi: 10.1038/nmeth.1778.
Koboldt, D.C.et al., "The next-generation sequencing revolution and its impact on genomics," Cell 2013, 155(1), 27-38.
Koboldt, et al. Massively parallel sequencing approaches for characterization of structural variation. Aug. 12, 2011. Methods Mol Biol. 2012;838:369-84. doi: 10.1007/978-1-61779-507-7_18.
Kolble, et al. Microsatellite alterations in serum DNA of patients with colorectal cancer. Lab Invest. Sep. 1999;79(9):1145-50.
Konig, et al. iCLIP reveals the function of hnRNAP particles in splicing at individual nucleotide resolution, Jul. 2010, Nature Structural & Molecular Biology, 17(7):909-916.

(56) References Cited

OTHER PUBLICATIONS

Kopreski, et al. Detection of mutant K-ras DNA in plasma or serum of patients with colorectal cancer. Br J Cancer. 1997;76(10):1293-9.
Korbel, J.O. et al., "Paired-end mapping reveals extensive structural variation in the human genome," Science 2007, 318(5849), 420-426.
Koyanagi, et al. Association of circulating tumor cells with serum tumor-related methylated DNA in peripheral blood of melanoma patients. Cancer Res. Jun. 15, 2006;66(12):6111-7.
Krimmel, J.D. et al., "Ultra-deep sequencing detects ovarian cancer cells in peritoneal fluid and reveals somatic TP53 mutations in noncancerous tissues," Proc. Natl. Acad. Sci. USA 2016, 113(21), 6005-6010.
Kukita, Y. et al. "High-fidelity target sequencing of individual molecules identified using barcode sequences: de novo detection and absolute quantitation of mutations in plasma cell-free DNA from cancer patients" DNA Research (2015) 22(4):269-277.
Lam, et al. Plasma DNA as a prognostic marker for stroke patients with negative neuroimaging within the first 24 h of symptom onset. Resuscitation. Jan. 2006;68(1):71-8. Epub Dec. 1, 2005.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi:10.1371/journal.pone.0140712.
Larson, et al. A single molecule view of gene expression. Trends Cell Biol. Nov. 2009;19(11):630-7. Epub Oct. 8, 2009.
Leary, et al. Detection of chromosomal alterations in the circulation of cancer patients with whole-genome sequencing. Sci Transl Med. Nov. 28, 2012;4(162):162ra154. doi: 10.1126/scitranslmed.3004742.
Leary, et al. Development of personalized tumor biomarkers using massively parallel sequencing. Sci Transl Med. Feb. 24, 2010;2(20):20ra14. doi: 10.1126/scitranslmed.3000702.
Lecomte, et al. Detection of free-circulating tumor-associated DNA in plasma of colorectal cancer patients and its association with prognosis Int J Cancer. Aug. 10, 2002;100(5):542-8.
Ledergerber, C. et al., "Base-calling for next-generation sequencing platforms," Brief Bioinform. 2011 12(5), 489-497.
Leon, et al. Free DNA in the serum of cancer patients and the effect of therapy. Cancer Res. Mar. 1977;37(3):646-50.
Leung, et al. Plasma Epstein-Barr viral deoxyribonucleic acid quantitation complements tumor-node-metastasis staging prognostication in nasopharyngeal carcinoma. J Clin Oncol. Dec. 1, 2006;24(34):5414-8.
Li, et al. Mapping short DNA sequencing reads and calling variants using mapping quality scores. Genome Res. Nov. 2008;18(11):1851-8. doi: 10/1101/gr/078212.108. Epub Aug. 19, 2008.
Li, et al. Structure-independent and quantitative ligation of single-stranded DNA. Anal Biochem. Feb. 15, 2006;349(2):242-6. Epub Nov. 18, 2005.
Li, H. et al., "Fast and accurate short read alignment with Burrows-Wheeler transform," Bioinformatics 2009, 25(14), 1754-1760.
Liang, K-C. et al., "Bayesian basecalling for DNA sequence analysis using hidden Markov models," IEE/ACM Trans. Comput. Biol. Bioinform. 2007 4(3), 430-440.
Liao, G.J.W. et al., "Targeted massively parallel sequencing of maternal plasma DNA permits efficient and unbiased detection of fetal alleles," Clin. Chem. 2011, 57(1), 92-101.
Lizardi, et al. Mutation detection and single-molecule counting using isothermal rolling-circle amplification. Nat Genet. Jul. 1998;19(3):225-32.
Lo, et al. Quantitative Analysis of Cell-free Epstein-Barr Virus DNA in Plasma of Patients with Nasopharyngeal Carcinoma, Cancer Research, 59(6):1188-1191 (Mar. 1999).
Lo, Y.M.D et al., "Quantitative analysis of fetal DNA in maternal plasma and serum: implications for noninvasive prenatal diagnosis," Am. J. Hum. Genet. 1998, 62(4), 768-775.
Lo, Y.M.D. et al. "Maternal Plasma DNA Sequencing Reveals the Genome-Wide Genetic and Mutational Profile of the Fetus," Sci Transl Med (2010) 2(61):1-13.
Lockhart, et al. Expression monitoring by hybridization to high-density oligonucleotide arrays. Nature Biotechnology, 14: 1675-1680 (1996).
Lodes, et al. Novel Chimera-Free, High Efficiency Library Preparation for NGS Platforms.Poster. Presented at the Plant & Animal Genome XX Conference. San Diego, California. Jan. 14-18, 2012. 1 page.
Lucito, et al. Detecting gene copy number fluctuations in tumor cells by microarray analysis of genomic representations. Genome Res. Nov. 2000;10(11):1726-36.
Lucito, et al. Representational Oligonucleotide Microarray Analysis: A High-Resolution Method to Detect Genome Copy Number Variation. Genome Research (2003), 13: 2291-2305.
Lunter, G. et al., "Stampy: A statistical algorithm for sensitive and fast mapping of Illumina sequence reads," Genome Res. 2011, 21(6):936-939.
Maamar, et al. Noise in Gene Expression Determines Cell Fate in Bacillus subtilis. Science, 317: 526-529 (2007).
Mahmud, et al. Fast MCMC sampling for hidden Markov Models to determine copy number variations. BMC Bioinformatics. Nov. 2, 2011;12:428. doi: 10.1186/1471-2105-12-428.
Makrigiorgos, et al., A PCR-Based amplification method retaining quantative difference between two complex genomes. Nature Biotech, vol. 20, No. 9, pp. 936-939 (Sep. 2002).
Mamanova, L. et al., "Target-enrichment strategies for next-generation sequencing," Nat. Methods 2010, 7(2), 111-118.
Mandel, et al. Les acides nucleiques du plasma sanguin chez l'homme. C R Seances Soc Biol Fil. Feb. 1948;142(3-4):241-3.
Marsit, et al. Epigenetic profiling reveals etiologically distinct patterns of DNA methylation in head and neck squamous cell carcinoma. Carcinogenesis. Mar. 2009;30(3):416-22. doi: 10.1093/carcin/bgp006. Epub Jan. 6, 2009.
McCloskey, et al. Encoding PCR products with batch-stamps and barcodes. Biochem Genet. Dec. 2007;45(11-12):761-7. Epub Oct. 23, 2007.
McKernon, K.J. et al., "Sequence and structural variation in a human genome uncovered by short-read, massively parallel ligation sequencing using two-base encoding," Genome Res. 2009, 19(9), 1527-1541.
Medvedev, et al. Detecting copy number variation with mated short reads. Genome Res. Nov. 2010;20(11):1613-22. doi: 10 1101/gr. 106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Meldrum, et al. Next generation sequencing for cancer diagnostics: a practical perspective. Clin Biochem Rev. Nov. 2011;32(4):177-95.
Mertes, F. et al. "Targeted enrichment of genomic DNA regions for next-generation sequencing" Brief Functional Genomics (2011) 10(6):374-386.
Metzker, M.L. "Sequencing technologies—the next generation" Nature Reviews Genetics (2010) 11:31-46.
Meyer, M. et al. "Illumina sequencing library preparation for highly multiplexed target capture and sequencing," Cold Spring Harb. Protoc. 2010, (6), prot5448.
Meyerson, M. et al. "Advances in understanding cancer genomes through second-generation sequencing" Nature Reviews Genetics (2010) 11:685-696.
Milbury, et al. "Enabling Clinical Cancer Genomics for Rare Mutations: COLD-PCR Magnifies Mutations Prior to Targeted Amplicon Re-Sequencing". Clin Chem. Mar. 2012;58(3):580-9. doi: 10.1373/clinchem.2011.176198. Epub Dec. 21, 2011.
Miner, et al. Molecular barcodes detect redundancy and contamination in hairpin-bisulfite PCR. Nucleic Acids Res. Sep. 30, 2004;32(17):e135.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitelman, F. et al. "The impact of translocations and gene fusions on cancer causation" Nature Rev. Cancer (2007) 7(4):233-245.
Mohan, et al.,Changes in colorectal carcinoma genomes under anti-EGFR therapy identified by whole-genome plasma DNA sequenc-

(56) References Cited

OTHER PUBLICATIONS ing.,PLoS Genet,doi: 10.1371/journal.pgen.1004271. eCollection 2014.,Mar. 27, 2014,10(3), e1004271.
Mori, et al. Predictive utility of circulating methylated DNA in serum of melanoma patients receiving biochemotherapy. J Clin Oncol. Dec. 20, 2005;23(36):9351-8.
Morrissy, A.S. et al. "Next-generation tag sequencing for cancer gene expression profiling" Genome Research (2009) 19(10): 1825-1835.
Mortazavi, et al. Mapping and quantifying mammalian transcriptomes by RNA-Seq. Nat. Methods. 2008; 5, 621-628.
Narayan, et al. Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012.
Nawroz, et al. Microsatellite alterations in serum DNA of head and neck cancer patients. Nat Med. Sep. 1996;2(9):1035-7.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Ng, S.B., et al., "Targeted capture and massively parallel sequencing of 12 human exomes," Nature 2009, 461(7261), 272-276.
Nielsen, R. et al. "Genotype and SNP calling from next-generation sequencing data" Nature Reviews Genetics (2011) 12(6):443-451.
Nord, et al. Accurate and exact CNV identification from targeted high-throughput sequence data. BMC Genomics. Apr. 12, 2011;12:184.
Ogino, et al. Quantification of PCR bias caused by a single nucleotide polymorphism in SMN gene dosage analysis. J Mol Diagn. Nov. 2002;4(4):185-90.
Pacific Biosciences. Template Preparation and Sequencing Guide. Publication date: Oct. 14, 2014. Pacific Biosciences website http://www.pacificbiosciences.com/support/pubmap/documentation.html.
Pan, et al. Loss of heterozygosity patterns provide fingerprints for genetic heterogeneity in multistep cancer progression of tobacco smoke-induced non-small cell lung cancer. Cancer Res. Mar. 1, 2005;65(5):1664-9.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Parkinson, N.J. et al., "Preparation of high-quality next-generation sequencing libraries from picogram quantities of target DNA," Genome Res. 2012, 22(1), 125-133.
Paweletz, C.P. et al. "Bias-corrected targeted next-generation sequencing for rapid, multiplexed detection of actionable alterations in cell-free DNA from advanced lung cancer patients" Clin Cane Res (2016) 22(4):915-922.
Pel, J. et al. "Duplex proximity sequencing (pro-seq): A method to improve DNA sequencing accuracy without the cost of molecular barcoding redundancy" bioRxiv (2017) https://doi.org/10.1101/163444.
Perakis, S. et al. "Advances in Circulating Tumor DNA Analysis" Adv Clin Chem (2017) pp. 1-81.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Pihlak, et al. Rapid genome sequencing with short universal tiling probes. Nature Biotechnology, 26: 676-684 (2008).
Pinkel, et al. Comparative Genomic Hybridization. Annual Review of Genomics and Human Genetics, 6: 331-354 (2005).
Umetani et al. Prediction of Breast Tumor Progression by Integrity of Free Circulating DNA in Serum. Journal of Clinical Oncology 24(26):4270-4276 (Sep. 10, 2006).
U.S. Appl. No. 61/384,001, filed Sep. 17, 2010.
U.S. Appl. No. 61/432,119, filed Jan. 12, 2011.
Utting, et al. Microsatellite analysis of free tumor DNA in urine, serum, and plasma of patients: a minimally invasive method for the detection of bladder cancer Clin Cancer Res. Jan. 2002;8(1):35-40.

Van Houten, et al. Mutated p53 as a molecular marker for the diagnosis of head and neck cancer. J Pathol. Dec. 2002;198(4):476-86.
Van Orsouw, N. et al. "Complexity Reduction of Polymorphic Sequences (CRoPSTM): A Novel Approach for Large-Scale Polymorphism Discovery in Complex Genomes" PLoS One (2007) 11(e1172):1-10.
Vasyukhin, V. et al., "K-Ras Point Mutations in the Blood Plasma DNA of Patients with Colorectal Tumors" Challenges of Modern Medicine, 141-150 (Verna and Shamoo eds, 1994).
Velculescu, et al. Characterization of the Yeast Transcriptome. Cell, 88:243-251 (1997).
Velculescu, et al. Serial Analysis of Gene Expression. Science, 270:484-487 (1995).
Vogelstein, et al. Digital PCR. Proc. Natl. Acad. Sci., 96(16): 9236-9241(1999).
Wagle, N. et al., "High-throughput Detection of actionable Genomic alterations in clinical tumor samples by targeted, Massively Parallel sequencing," Cancer Discov. 2012, (2)1:82-93.
Walker, et al. Isothermal in vitro amplification of DNA by a restriction enzyme/DNA polymerase system. Proc Natl Acad Sci USA. Jan. 1, 1992;89(1):392-6.
Walsh, et al. Detection of inherited mutations for breast and ovarian cancer using genomic capture and massively parallel sequencing. Proc Natl Acad Sci USA. Jul. 13, 2010; 107(28):12629-33. doi: 10.1073/pnas.1007983107. Epub Jun. 28, 2010.
Wang, et al. iCLIP predicts the dual splicing effects of TIA-RNA interactions, Oct. 2010, PLoS Biol, 8(10):e1000530.
Wang, et al. Molecular detection of APC, K- ras, and p53 mutations in the serum of colorectal cancer patients as circulating biomarkers. World J Surg. Jul. 2004;28(7):721-6. Epub Jun. 8, 2004.
Wang, et al. RNA-Seq: a revolutionary tool for transcriptomics. Nature Reviews Genetics, 10: 57-63 (2009).
Wang, T.L. et al. "Digital Karyotyping" PNAS (2002) 99(25):16156-16161.
Wang, Y. et al., "Detection of somatic mutations and HPV in the saliva and plasma of patients with head and neck squamous cell carcinomas," Sci. Transl. Med. 2015, 7(293):293ra104.
Wang, Y. et al., "Detection of tumor-derived DNA in cerebrospinal fluid of patients with primary tumors of the brain and spinal cord," Proc. Natl. Acad. Sci. USA 2015, 112(31), 9704-9709.
Wang, Y. et al., "Diagnostic potential of tumor DNA from ovarian cyst fluid," eLife 2016, 5:e15175.
Weber, et al. A real-time polymerase chain reaction assay for quantification of allele ratios and correction of amplification bias Anal Biochem. Sep. 15, 2003;320(2):252-8.
Wheeler, D.A. et al., "The complete genome of an individual by massively parallel DNA sequencing," Nature 2008, 452(7189), 872-876.
Williford, A. et al., "Gene Fusion," eLS 2013, 1-8.
Wittes, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in *Saccharomyces cerevisiae*. Nature Biotechnology, 15:1359-1367 (1997).
Wojdacs, et al. Primer design versus PCR bias in methylation independent PCR amplifications. Epigenetics. May 16, 2009;4(4):231-4. Epub May 14, 2009.
Wood, et al. The genomic landscapes of human breast and colorectal cancers. Science. Nov. 16, 2007;318(5853):1108-13. Epub Oct. 11, 2007.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Xi, et al. Copy number variation detection in whole-genome sequencing data using the Bayesian information criterion. Proc Natl Acad Sci USA Nov. 15, 2011; 108(46):E1128-36 doi: 10.1073/pnas.1110574108. Epub Nov. 7, 2011.
Yandell, et al. A probabilistic disease-gene finder for personal genomes. Genome Res. Sep. 2011;21(9):1529-42. doi: 10 1101/gr.123158.111. Epub Jun. 23, 2011.

(56) References Cited

OTHER PUBLICATIONS

Yang, et al., EGFR gene copy number as a predictive biomarker for the treatment of metastatic colorectal cancer with anti-EGFR monoclonal antibodies: a meta-analysis.,J Hematol Oncol, Aug. 16, 2012,5:52,1-9.
Yang. Simple binary segmentation frameworks for identifying variation in DNA copy number. BMC Bioinformatics. Oct. 30, 2012;13:277. doi: 10.1186/1471-2105-13-277.
Ye, et al. Fluorescent microsphere-based readout technology for multiplexed human single nucleotide polymorphism analysis and bacterial identification. Human Mutation, 17(4): 305-316 (2001).
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang et al. "Comprehensive One-Step Molecular Analysis of Mitochondrial Genome by Massively Parallel Sequencing" Clinical Chem (2012) 58(9):1322-1331.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosome 18q loss and vascularinvasion. Nature Biotechnology, 19: 78-81 (2001).
Daser, et al. "Interrogation of genomes by molecular copy-number counting (MCC)." Nature Methods, 3(6): 447-453 (2006).
De Saizieu, et al. "Bacterial transcript imaging by hybridization of total RNA to oligonucleotide arrays." Nature Biotechnology, 16: 45-48 (1998).
Diehl et al. Circulating mutant DNA to assess tumor dynamics. Nat Med 14(9):985-990 (2008).
Diehl, et al. Detection and quantification of mutations in the plasma of patients with colorectal tumors. Proc Natl Acad Sci US A. Nov. 8, 2005; 102(45):16368-73. Epub Oct. 28, 2005.
Diehl, F. et al., "Analysis of Mutations in DNA Isolated From Plasma and Stool of Colorectal Cancer Patients," Gastroenterology (2008) 135(2):489-498.
Ding, L. et al., "Analysis of next-generation genomic data in cancer: accomplishments and challenges," Hum Mol. Genet. 2010 19(R2), R188-R196.
Duncan, D.L. et al. "Next-Generation Sequencing in the Clinical Laboratory" Diagnostic Molecular Pathology: A Guide to Applied Molecular Testing 25-33 (Coleman and Tsongalis eds., 1st ed. 2016).
Ehrich, et al. Noninvasive detection of fetal trisomy 21 by sequencing of DNA in maternal blood: a study in a clinical setting. Am J Obstet Gynecol. Mar. 2011;204(3):205.e1-11. doi: 10.1016/j.ajog.2010.12.060. Epub Feb. 18, 2011.
Eisenmann, et al. 5q-myelodysplastic syndromes: chromosome 5q genes direct a tumor-suppression network sensing actin dynamics. Oncogene. Oct. 1, 2009;28(39):3429-41. doi: 10.1038/onc.2009.207. Epub Jul. 13, 2009.
Elshire, et al. A robust, simple genotyping-by-sequencing (GBS) approach for high diversity species. PLoS One. May 4, 2011;6(5):e19379. doi: 10.1371/journal.pone.0019379.
Fan, et al. "Microfluidic digital PCR enables rapid prenatal diagnosis of fetal aneuploidy." Am Obstet Gynecol. 2009; 200:543.e1-543.e7.
Fan, et al. "Parallel Genotyping of Human SNPs Using Generic High-density Oligonucleotide Tag Arrays." Genome Research, 10: 853-860 (2000).
Fan, et al. Noninvasive diagnosis of fetal aneuploidy by shotgun sequencing DNA from maternal blood. Proc Natl Acad Sci USA. Oct. 21, 2008; 105(42):16266-71. Epub Oct. 6, 2008.
Fan, et al. Non-invasive prenatal measurement of the fetal genome. Nature. Jul. 19, 2012;487(7407):320-4. doi: 10.1038/nature 11251.

Fleischhacker, M. et al. "Circulating nucleic acids (CNAs) and cancer—A survey" Biochimica et Biophysica Acta (2007) 1775:181-232.
Fonatsch, C. The role of chromosome 21 in hematology and oncology. Genes Chromosomes Cancer. Jun. 2010;49(6):497-508. doi: 10.1002/gcc.20764.
Fong, S.L. et al. "Comparison of 7 Methods for Extracting Cell-Free DNA from Serum Samples of Colorectal Cancer Patients" Clinical Chem (2009) 55(3):587-598.
Forshew, T. et al. "Noninvasive Identification and Monitoring of Cancer Mutations by Targeted Deep Sequencing of Plasma DNA" Sci Transl Med (2012) 4(136) ra68.
Forster, et al. From next-generation sequencing alignments to accurate comparison and validation of single-nucleotide variants: the pibase software. Nucleic Acids Res. Jan. 7, 2013;41(1):e16. doi: 10.1093/nar/gks836. Epub Sep. 10, 2012.
Fournie, et al. Plasma DNA as a marker of cancerous cell death. Investigations in patients suffering from lung cancer and in nude mice bearing human tumours. Cancer Lett. May 8, 1995;91(2):221-7.
Freeman, et al. Profiling the T-cell receptor beta-chain repertoire by massively parallel sequencing. Genome Res. Oct. 2009;19(10):1817-24. doi: 10.1101/gr.092924.109. Epub Jun. 18, 2009.
Fu, et al. Counting individual DNA molecules by the stochastic attachment of diverse labels. Proc Natl Acad Sci U S A. May 31, 2011;108(22):9026-31. Epub May 11, 2011.
Fujiwara, et al. Identification of epigenetic aberrant promoter methylation in serum DNA is useful for early detection of lung cancer. Clin Cancer Res. Feb. 1, 2005;11(3):1219-25.
Fujiwara, et al. Plasma DNA microsatellites as tumor-specific markers and indicators of tumor progression in melanoma patients Cancer Res. Apr. 1, 1999;59(7):1567-71.
Genome Analyzer IIx Systems Specification Sheet (2009).
Gerry, et al. Universal DNA microarray method for multiplex detection of low abundance point mutations. Journal of Molecular Biology, 292(2): 251-262 (1999).
Gillespie. Exact stochastic simulation of coupled chemical reactions. The Journal of Physical Chemistry, 81(25):2340-2361 (1977).
Gordian, et al. Serum free circulating DNA is a useful biomarker to distinguish benign versus malignant prostate disease. Cancer Epidemiol Biomarkers Prev. Aug. 2010;19(8):1984-91. doi: 10.1158/1055-9965.EPI-10-0287. Epub Jul. 20, 2010.
Gordon, D.J. et al., "Causes and consequences of aneuploidy in cancer," Nat. Rev. Genet. 2012 13(3), 189-203.
Gormally, et al. Amount of DNA in plasma and cancer risk: a prospective study. Int J Cancer. Sep. 20, 2004;111(5):746-9.
Grant, et al. SNP genotyping on a genome-wide amplified DOP-PCR template. Nucleic Acids Res. Nov. 15, 2002;30(22):e25.
Gregory et al. "Targeted Single Molecule Mutation Detection with Massively Parallel Sequencing" Nucleic Acids Research (2015) 44(3):2-11.
Grutzmann, et al. Sensitive detection of colorectal cancer in peripheral blood by septin 9 DNA methylation assay. PLoS One. 2008;3(11):e3759. doi: 10.1371/journal.pone.0003759. Epub Nov. 19, 2008.
Gundry, et al. "Direct mutation analysis by high-throughput sequencing: from gremlin to low-abundant, somatic variants" Mutat Res Jan. 3, 2012; 729(1-2):1-15. doi: 10.1016/mrfmmm.2011.10.001. Pub Oct. 12, 2011.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Hacia, et al. Determination of ancestral alleles for human single-nucleotide polymorphisms using high-density oligonucleotide arrays. Nature Genetics, 22: 164-167 (1999).
Hafner, et al., RNA-ligase-dependent biases in miRNA representation in deep-sequenced small RNA eDNA libraries, RNA Sep. 1, 2011, 17(9):1697-1712.
Hall, A., Short-Read DNA Sequence Alignmnet with Custom Designed FPGA-based Hardware, Thesis 2010.
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

(56) References Cited

OTHER PUBLICATIONS

Hensel, et al. Simultaneous identification of bacterial virulence genes by negative selection. Science. Jul. 21, 1995;269(5222):400-3.

Hiatt, et al. Parallel, tag-directed assembly of locally derived short sequence reads. Nat Methods. Feb. 2010;7(2):119-22. doi: 10.1038/nmeth.1416. Epub Jan. 17, 2010.

Hiatt, et al. Single molecule molecular inversion probes for targeted, high-accuracy detection of low-frequency variation. Genome Res May 2013;23(5):843-54. doi: 10.1101/gr.147686.112. Epub Feb. 4, 2013.

Hibi, et al. Molecular detection of genetic alterations in the serum of colorectal cancer patients. Cancer Res. Apr. 1, 1998;58(7):1405-7.

HiSeq 2000 User Guide (2010).

Holdenrieder, et al. Circulating nucleosomes and cytokeratin 19-fragments in patients with colorectal cancer during chemotherapy. Anticancer Res. May-Jun. 25, 2005;(3A):1795-801.

Holies, et al. A stochastic approach to count RNA molecules using DNA sequencing methods. 2003, Lecture Notes in Computer Science, vol. 2812, pp. 55-62.

Hollstein, M. et al. "p53 mutations in human cancers" Science (1991) 253(5015):49-53.

Hoque, et al. Detection of aberrant methylation of four genes in plasma DNA for the detection of breast cancer. J Clin Oncol. Sep. 10, 2006;24(26):4262-9. Epub Aug. 14, 2006.

Howe, et al. Retinoblastoma growth suppressor and a 300-kDa protein appear to regulate cellular DNA synthesis. Proc Natl Acad Sci U S A. Aug. 1990;87(15):5883-7.

Hug, et al. Measurement of the number of molecules of a single mRNA species in a complex mRNA preparation. J Theor Biol. Apr. 21, 2003;221(4):615-24.

| Point Mutations (SNVs) (70 Genes) | | | | | Amplifications (CNVs) (16 Genes) | | | Fusions (6 Genes) | Indels (3 Genes) |
|---|---|---|---|---|---|---|---|---|---|
| AKT1 | ALK | APC | AR | ARAF | ARID1A | AR | BRAF | ALK | EGFR* |
| ATM | BRAF | BRCA1 | BRCA2 | CCND1 | CCND2 | CCNE1 | CDK4 | FGFR2 | ERBB2* |
| CCNE1 | CDH1 | CDK4 | CDK6 | CDKN2A | CDKN2B | CDK6 | EGFR | FGFR3 | MET** |
| CTNNB1 | EGFR | ERBB2 | ESR1 | EZH2 | FBXW7 | ERBB2 | FGFR1 | NTRK1 | |
| FGFR1 | FGFR2 | FGFR3 | GATA3 | GNA11 | GNAQ | FGFR2 | KIT | RET | |
| GNAS | HNF1A | HRAS | IDH1 | IDH2 | JAK2 | KRAS | MET | ROS1 | |
| JAK3 | KIT | KRAS | MAP2K1 | MAP2K2 | MET | MYC | PDGFRA | | |
| MLH1 | MPL | MYC | NF1 | NFE2L2 | NOTCH1 | PIK3CA | RAF1 | | *exons 19 & 20 |
| NPM1 | NRAS | NTRK1 | PDGFRA | PIK3CA | PTEN | | | | *exons 19 & 20 |
| PTPN11 | RAF1 | RB1 | RET | RHEB | RHOA | | | | **exon 14 skipping |
| RIT1 | ROS1 | SMAD4 | SMO | SRC | STK11 | | | | |
| TERT | TP53 | TSC1 | VHL | | | | | | |

FIG. 1

METHODS TO DETERMINE TUMOR GENE COPY NUMBER BY ANALYSIS OF CELL-FREE DNA

CROSS-REFERENCE

This application is a continuation of U.S. patent application Ser. No. 15/442,993, filed Feb. 27, 2017, which is a continuation application of International Patent Application No. PCT/US2016/067356, filed Dec. 16, 2016, which application claims priority to U.S. Provisional Application No. 62/269,051, filed Dec. 17, 2015, each of which is hereby incorporated by reference in its entirety.

BACKGROUND

Cancer is caused by the accumulation of mutations within an individual's normal cells, at least some of which result in improperly regulated cell division. Such mutations commonly include copy number variations, in which the number of copies of a gene within a tumor genome increases or decreases relative to the subject's noncancerous cells.

Detecting and characterizing copy number variation in tumor cells is used to monitor tumor progression, predict patient outcome, and refine treatment choices. Conventional methods, however, are performed on cellular samples that are often obtained by painful and time-intensive biopsies. Such biopsies also can often only examine a fraction of the tumor cells within a subject, and thus are not always representative of the population of tumor cells. There is a need for simpler, more rapid tests for copy number variation in tumors that do not require cellular biopsies, fluorescent in situ hybridization (FISH), comparative genome hybridization arrays, or quantitative fluorescent polymerase chain reaction (PCR) assays.

A particular challenge in determining copy number variation using sequencing data is that genetic loci will exhibit variance in their depth of coverage for reasons unrelated to true copy number. For example, amplification efficiency, PCR efficiency, and guanine-cytosine content can cause differing depths of coverage even for individual genetic loci present in the sample at the same copy number. Improved methods of removing bias due to such effects are needed to improve copy number detection.

SUMMARY

There exists a considerable need for improved methods to detect copy number variation in tumor cells from samples derived from cell-free bodily fluids. The present invention addresses this need and provides additional advantages. In one aspect, the present disclosure provides a method comprising: (a) obtaining sequencing reads of deoxyribonucleic acid (DNA) molecules of a cell-free bodily fluid sample of a subject; (b) generating from the sequence reads a first data set comprising for each genetic locus in a plurality of genetic loci a quantitative measure related to sequencing read coverage ("read coverage"); (c) correcting the first data set by performing saturation equilibrium correction and probe efficiency correction; (d) determining a baseline read coverage for the first data set, wherein the baseline read coverage relates to saturation equilibrium and probe efficiency; and (e) determining a copy number state for each genetic locus in the plurality of genetic loci relative to the baseline read coverage. In some embodiments, the first data set comprises, for each genetic locus in a plurality of genetic loci, a quantitative measure related to (i) guanine-cytosine content ("GC content") of the genetic locus. In some embodiments, the method comprises, prior to (c), removing from the first data set genetic loci that are high-variance genetic loci, wherein removing comprises: (i) fitting a model relating the quantitative measures related to guanine-cytosine content and the quantitative measures of sequencing read coverage of the genetic loci; and (ii) removing from the genetic loci at least 10% of the genetic loci, wherein the removing the genetic loci comprises removing genetic loci that most differ from the model, thereby providing the first data set of baselining genetic loci. In some embodiments, the method comprises removing at least 45% of the genetic loci.

In some embodiments, performing saturation equilibrium correction comprises transforming the first data set of baselining data genetic loci into a saturation corrected data set by: (i) determining for each genetic locus from the first data set of baselining genetic loci a quantitative measure related to the probability that a strand of DNA molecule from the sample derived from the genetic locus is represented within the sequencing reads; (ii) determining a first transformation for the read coverage by relating the read coverage of the first data set of baselining genetic loci to both the GC content of the first data set of baselining genetic loci and the quantitative measure related to the probability that a strand of DNA derived from each locus in the first data set of baselining genetic loci is represented within the sequencing reads; and (iii) applying the first transformation to the read coverage of each genetic locus from the first data set of baselining genetic loci to provide the saturation corrected data set, wherein the saturation corrected data set comprises a first set of transformed read coverages of the first data set of baselining genetic loci.

In some embodiments, determining the first transformation comprises (i) determining a measure related to central tendency of the read coverage of the first data set of baselining genetic loci; (ii) determining a function that fits the measure related to central tendency of the read coverage of the first data set of baselining genetic loci based on the GC content of the genetic locus and the quantitative measure related to the probability that a strand of DNA derived from the genetic locus is represented within the sequencing reads; and (iii) for each genetic locus of the first data set of baselining genetic loci, determining a difference between the read coverage predicted by the function and the read coverage, wherein the difference is the transformed read coverage. In some embodiments, the function is a surface approximation. In some embodiments provided herein, the surface approximation is a two-dimensional second degree polynomial.

In some embodiments, performing probe efficiency correction comprises transforming the saturation corrected data set into a probe efficiency corrected data set by: (i) removing from the saturation corrected data set genetic loci that are high-variance genetic loci with respect to the first set of transformed read coverages, thereby providing a second data set of baselining genetic loci; (ii) determining a second transformation for the first set of transformed read coverages related to the probe efficiency of the second data set of baselining genetic loci; and (iii) transforming the first set of transformed read coverages of the second data set of baselining genetic loci with the second transformation, thereby providing the probe efficiency corrected data set, wherein the probe efficiency corrected data set comprises a second set of transformed read coverages of the second data set of baselining genetic loci. In some embodiments, removing from the first data set genetic loci that are high-variance genetic loci comprises: (i) fitting a model relating the GC content and the first set of transformed read coverages of the saturation corrected data set; and (ii) removing from saturation corrected data set at least 10% of the genetic loci, wherein the removing the genetic loci comprises removing genetic loci that most differ from the model, thereby providing the second data set of baselining genetic loci. In some embodiments provided herein, the removing is at least 45% of the genetic loci.

In some embodiments, probe efficiency is determined by performing the saturation equilibrium correction on one or more reference samples, wherein the probe efficiency is the transformed read coverage obtained by performing the saturation equilibrium correction. In some embodiments, one or more reference samples are cell-free bodily fluid samples from a subject without cancer. In some embodiments provided herein the one or more reference samples are cell-free bodily fluid samples from a subject with cancer, wherein the corresponding genetic locus has not undergone copy number alteration.

In some embodiments, determining the second transformation comprises (i) fitting the probe efficiency determined for the genetic loci from the one or more reference samples to the first set of read coverages from the second data set of baselining genetic loci; (ii) dividing the transformed read coverages of each genetic locus of the second data set of baselining genetic loci by a predicted probe efficiency based on the fitting of (i). In some embodiments, the method further comprises: (f) determining a third transformation for the second set of transformed read coverages by relating the transformed read coverages of the second data set of baselining genetic loci to both the GC content of the second data set of baselining genetic loci and the quantitative measure related to the probability that a strand of DNA derived from the each locus in the second data set of baselining genetic loci is represented within the sequencing reads; and (g) applying the third transformation to the second set of transformed read coverages to provide a fourth data set, wherein the fourth data set comprises a third set of transformed quantitative read coverages.

In some embodiments, the DNA of the cell-free bodily fluid sample is enriched for the set of genetic loci using one or more oligonucleotide probes that are complementary to at least a portion of the genetic locus from the set of genetic loci. In some embodiments, the GC content of each genetic locus from the set of genetic loci is a measure related to central tendency of guanine-cytosine content of the one or more oligonucleotide probes that are complementary to at least a portion of the genetic locus from the set of genetic loci. In some embodiments, the read coverage of the genetic locus is a measure related to central tendency of the read coverage of regions of the genetic locus corresponding to the one or more oligonucleotide probes. In some embodiments, the performing saturation equilibrium correction and the performing probe efficiency correction comprises fitting a Langmuir model, wherein the Langmuir model comprises probe efficiency (K) and saturation equilibrium constant (Isat). In some embodiments, K and Isat are determined empirically for each oligonucleotide probe in the one or more oligonucleotide probes. In some embodiments, the performing saturation equilibrium correction and performing probe correction comprises fitting the read coverages of the genetic loci to the Langmuir model assuming that the genetic loci are present in identical copy number states, thereby providing a baseline read coverage. In some embodiments, the identical copy number states are diploid.

In some embodiments the baseline rad coverage is a function dependent on the probe efficiency and the saturation equilibrium.

In some embodiments, determining a copy number state comprises comparing the read coverage of the genetic loci to the baseline read coverage. In some embodiments, the cell-free bodily fluid is selected from the group consisting of serum, plasma, urine, and cerebrospinal fluid. In some embodiments, the read coverage is determined by mapping the sequencing reads to a reference genome. In some embodiments, obtaining the sequencing reads comprises ligating adaptors to the DNA molecules from the cell-free bodily fluid from the subject. In some embodiments, the DNA molecules are duplex DNA molecules and the adaptors are ligated to the duplex DNA molecules such that each adaptor differently tags complementary strands of the DNA molecule to provide tagged strands. In some embodiments, determining the quantitative measure related to the probability that a strand of DNA derived from the genetic locus is represented within the sequencing reads comprises sorting sequencing reads into paired reads and unpaired reads, wherein (i) each paired read corresponds to sequence reads generated from a first tagged strand and a second differently tagged complementary strand derived from a double-stranded polynucleotide molecule in said set, and (ii) each unpaired read represents a first tagged strand having no second differently tagged complementary strand derived from a double-stranded polynucleotide molecule represented among said sequence reads in said set of sequence reads. In some embodiments, the method further comprises determining quantitative measures of (i) said paired reads and (ii) said unpaired reads that map to each of one or more genetic loci to determine a quantitative measure related to total double-stranded DNA molecules in said sample that map to each of said one or more genetic loci based on said quantitative measure related to paired reads and unpaired reads mapping to each locus. In some embodiments, the adaptors comprise barcode sequences.

In some embodiments, determining the read coverage comprises collapsing the sequencing reads based on position of the mapping of the sequencing reads to the reference genome and the barcode sequences. In some embodiments, the genetic loci comprise one or more oncogenes. In some embodiments, a method comprises determining that at least a subset of the baselining genetic loci has undergone copy number alteration in the tumor cells of the subject by determining relative quantities of variants within the baselining genetic loci for which the germline genome of the subject is heterozygous. In some embodiments, the relative quantities of the variants are not approximately equal. In some embodiments, baselining genetic loci for which the relative quantities of the variants are not approximately equal are removed from the baselining genetic loci, thereby providing allelic-frequency corrected baselining genetic loci. In some embodiments, the allelic-frequency corrected baselining genetic loci are used as the baselining loci in the methods of any one of the preceding claims.

In another aspect, the present disclosure provides a method comprising: receiving into memory sequencing reads of deoxyribonucleic acid (DNA) molecules of a cell-free bodily fluid sample of a subject; executing code with a computer processor to perform the following steps: generating from the sequence reads a first data set comprising for each genetic locus in a plurality of genetic loci a quantitative measure related to sequencing read coverage ("read coverage"); correcting the first data set by performing saturation equilibrium correction and probe efficiency correction;

determining a baseline read coverage for the first data set, wherein the baseline read coverage relates to saturation equilibrium and probe efficiency; and determining a copy number state for each genetic locus in the plurality of genetic loci relative to the baseline read coverage.

In another aspect, the present disclosure provides a system comprising: a network; a database comprising computer memory configured to store nucleic acid (e.g., DNA) sequence data which are connected to the network; a bioinformatics computer comprising a computer memory and one or more computer processors, which computer is connected to the network; wherein the computer further comprises machine-executable code which, when executed by the one or more computer processors, copies nucleic acid (e.g., DNA) sequence data stored on the database, writes the copied data to memory in the bioinformatics computer and performs steps including: generating from the nucleic acid (e.g., DNA) sequence data a first data set comprising for each genetic locus in a plurality of genetic loci a quantitative measure related to sequencing read coverage ("read coverage"); correcting the first data set by performing saturation equilibrium correction and probe efficiency correction; determining a baseline read coverage for the first data set, wherein the baseline read coverage relates to saturation equilibrium and probe efficiency; and determining a copy number state for each genetic locus in the plurality of genetic loci relative to the baseline read coverage. In some embodiments, the database is connected to a DNA sequencer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates exemplary oncogenes and targets for sequence capture probes.

FIG. 10A is from a subject without copy number alteration in tumor cells. FIG. 10B is from a subject with copy number alteration in tumor cells.

DETAILED DESCRIPTION

Definitions

Figure 2:
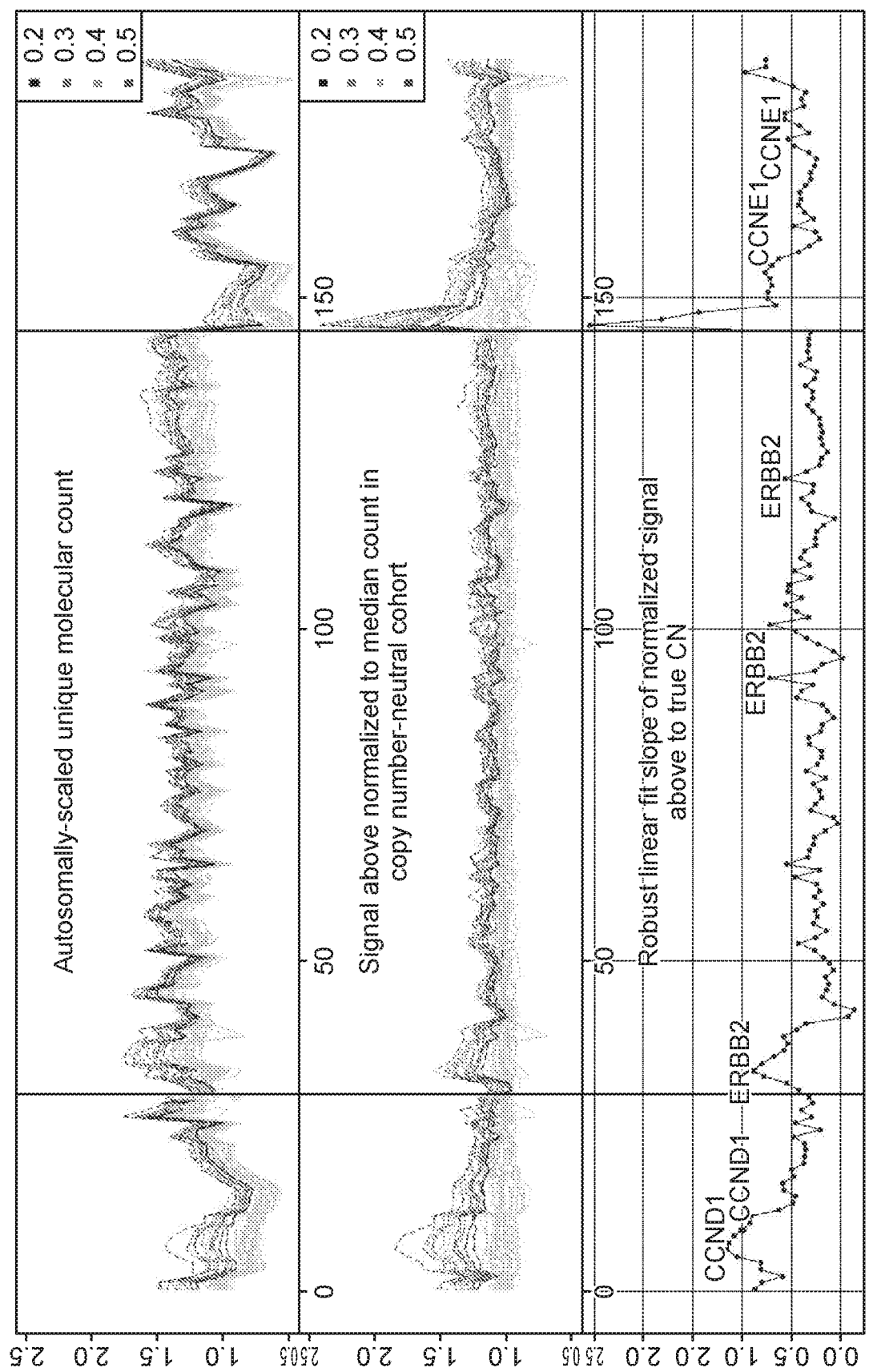
FIG. 2 illustrates gene-level signal versus theoretical copy number across three spike-in and probe-level signal variation across spike-in genes

The term "genetic variant," as used herein, generally refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The term "polynucleotide," as used herein, generally refers to a molecule comprising one or more nucleic acid subunits. A polynucleotide can include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a polynucleotide is deoxyribonucleic acid (DNA) or ribonucleic acid (RNA), or derivatives thereof. A polynucleotide can be single-stranded or double stranded.

The term "subject," as used herein, generally refers to an animal, such as a mammalian species (e.g., human) or avian (e.g., bird) species, or other organism, such as a plant. More specifically, the subject can be a vertebrate, a mammal, a mouse, a primate, a simian or a human. Animals include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes a human genome.

The terms "adaptor(s)", "adaptor(s)" and "tag(s)" are used synonymously throughout this specification. An adaptor or tag can be coupled to a polynucleotide sequence to be "tagged" by any approach including ligation, hybridization, or other approaches.

The term "library adaptor" or "library adaptor" as used herein, generally refers to a molecule (e.g., a polynucleotide) whose identity (e.g., sequence) can be used to differentiate polynucleotides in a biological sample (also "sample" herein).

The term "sequencing adaptor," as used herein, generally refers to a molecule (e.g., a polynucleotide) that is adapted to permit a sequencing instrument to sequence a target polynucleotide, such as by interacting with the target polynucleotide to enable sequencing. The sequencing adaptor permits the target polynucleotide to be sequenced by the sequencing instrument. In an example, the sequencing adaptor comprises a nucleotide sequence that hybridizes or binds to a capture polynucleotide attached to a solid support of a sequencing system, such as a flow cell. In another example, the sequencing adaptor comprises a nucleotide sequence that hybridizes or binds to a polynucleotide to generate a hairpin loop, which permits the target polynucleotide to be sequenced by a sequencing system. The sequencing adaptor can include a sequencer motif, which can be a nucleotide sequence that is complementary to a flow cell sequence of other molecule (e.g., polynucleotide) and usable by the sequencing system to sequence the target polynucleotide. The sequencer motif can also include a primer sequence for use in sequencing, such as sequencing by synthesis. The sequencer motif can include the sequence(s) needed to couple a library adaptor to a sequencing system and sequence the target polynucleotide.

As used herein the terms "at least", "at most" or "about", when preceding a series, refers to each member of the series, unless otherwise identified.

The term "about" and its grammatical equivalents in relation to a reference numerical value can include a range of values up to plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

The term "at least" and its grammatical equivalents in relation to a reference numerical value can include the reference numerical value and greater than that value. For example, the amount "at least 10" can include the value 10 and any numerical value above 10, such as 11, 100, and 1,000.

The term "at most" and its grammatical equivalents in relation to a reference numerical value can include the reference numerical value and less than that value. For example, the amount "at most 10" can include the value 10 and any numerical value under 10, such as 9, 8, 5, 1, 0.5, and 0.1.

The term "quantitative measure" refers to any measure of quantity including absolute and relative measures. A quantitative measure can be, for example, a number (e.g., a count), a percentage, a degree or a threshold.

The term "read coverage" refers to coverage by raw sequence reads or by processed sequence reads, such as unique molecular counts inferred from raw sequence reads.

The term "baseline read coverage" refers to expected read coverage of a probe in a sample comprising a diploid genome environment based on given probe parameters, such as GC content, probe efficiency, ligation efficiency, or pull down efficiency.

"Probe", as used herein, refers to a polynucleotide comprising a functionality. The functionality can be a detectable label (fluorescent), a binding moiety (biotin), or a solid support (a magnetically attractable particle or a chip).

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (Watson-Crick base pairing) with a second nucleic acid sequence (5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence.

"Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at the world wide web site: ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at the world wide web site: ebi.ac.uk/Tools/psa/emboss water/nucleotide.html, optionally with default settings). Optimal alignment may be assessed using any suitable parameters of a chosen algorithm, including default parameters.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

The term "stringent hybridization conditions" refers to conditions under which a polynucleotide will hybridize preferentially to its target subsequence, and to a lesser extent to, or not at all to, other sequences. "Stringent hybridization" in the context of nucleic acid hybridization experiments are sequence dependent, and are different under different environmental parameters. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays", Elsevier, New York.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

Stringent hybridization conditions include a buffer comprising water, a buffer (a phosphate, tris, SSPE or SSC buffer at pH 6-9 or pH 7-8), a salt (sodium or potassium), and a denaturant (SDS, formamide or tween) and a temperature of 37° C. –70° C., 60° C. –65° C.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

In one aspect, the present disclosure provides a method comprising: (a) obtaining sequencing reads derived from deoxyribonucleic acid (DNA) molecules of a cell-free bodily fluid sample of a subject; (b) generating a first data set, the first data set comprising, for each genetic locus in a plurality of genetic loci, a quantitative measure related to (i) guanine-cytosine content of the genetic locus and (ii) a quantitative measure related to sequencing read coverage of the genetic locus from the sequencing reads; (c) transforming the first data set into a second data set by: (i) removing from the first data set genetic loci that are high-variance genetic loci with respect to the quantitative measure related to sequencing read coverage, thereby providing a first set of remaining genetic loci; (ii) determining for each genetic locus from the first set of remaining genetic loci a quantitative measure related to the probability that a strand of DNA from the sample derived from the genetic locus is represented within the sequencing reads; (iii) determining a first transformation for the quantitative measure related to sequencing read coverage by relating the quantitative measure related to sequencing read coverage of the first set of remaining genetic loci to both the quantitative measure related to the GC content of the first set of remaining genetic loci and the quantitative measure related to the probability that a strand of DNA derived from the each locus in the first set of remaining genetic loci is represented within the sequencing reads; and (iv) applying the first transformation to the sequence read coverage of each genetic locus from the first set of remaining genetic loci to provide the second data set, wherein the second data set comprises a first set of transformed quantitative measures of sequencing read coverage of the first set of remaining genetic loci.

In some embodiments, the method further comprises transforming the second data set into a third data set by: (d) removing from the second data set genetic loci that are high-variance genetic loci with respect to the first set of transformed quantitative measures of sequencing read coverage, thereby providing a second set of remaining genetic loci; (e) determining a second transformation for the first set of transformed quantitative measures of sequencing read coverage related to the efficiency of the second set of remaining genetic loci; and (f) transforming the first set of transformed quantitative measures of sequencing read coverage of the second set of remaining genetic loci with the second transformation, thereby providing the third data set, wherein the third data set comprises a second set of transformed quantitative measures related to sequencing read coverage of the second set of remaining genetic loci of (d, i);

Obtaining Sequencing Reads from DNA Molecules of a Cell-Free Bodily Fluid from a Subject Obtaining sequencing reads from DNA molecules of a cell-free bodily fluid of a subject can comprise obtaining a cell-free bodily fluid. Exemplary cell-free bodily fluids are or can be derived from serum, plasma, blood, saliva, urine, synovial fluid, whole blood, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, or any other bodily fluids. A cell-free bodily fluid can be selected from the group consisting of plasma, urine, or cerebrospinal fluid. A cell-free bodily fluid can be plasma. A cell-free bodily fluid can be urine. A cell-free bodily fluid can be cerebrospinal fluid.

Nucleic acid molecules, including DNA molecules, can be extracted from cell-free bodily fluids. DNA molecules can be genomic DNA. DNA molecules can be from cells of healthy tissue of the subject. DNA molecules can be from noncancerous cells that have undergone somatic mutation. DNA molecules can be from a fetus in a maternal sample. The skilled worker will understand that, in embodiments wherein the DNA molecules are from a fetus in a maternal sample, a subject may refer to the fetus even though the sample is maternal. DNA molecules can be from precancerous cells of the subject. DNA molecules can be from cancerous cells of the subject. DNA molecules can be from cells within primary tumors of the subject. DNA molecules can be from secondary tumors of the subject. DNA molecules can be circulating DNA. The circulating DNA can comprise circulating tumor DNA (ctDNA). DNA molecules can be double-stranded or single-stranded. Alternatively, DNA molecule can comprise a combination of a double-stranded portion and a single-stranded portion. DNA molecules do not have to be cell-free. In some cases, the DNA molecules can be isolated from a sample. For example, DNA molecules can be cell-free DNA isolated from a bodily fluid, e.g., serum or plasma.

A sample can comprise various amounts of genome equivalents of nucleic acid molecules. For example, a sample of about 30 ng DNA can contain about 10,000 haploid human genome equivalents and, in the case of cfDNA, about 200 billion individual polynucleotide molecules. Similarly, a sample of about 100 ng of DNA can contain about 30,000 haploid human genome equivalents and, in the case of cfDNA, about 600 billion individual molecules.

Cell-free DNA molecules may be isolated and extracted from bodily fluids using a variety of techniques known in the art. In some cases, cell-free nucleic acids may be isolated, extracted and prepared using commercially available kits such as the Qiagen Qiamp® Circulating Nucleic Acid Kit protocol. In other examples, Qiagen Qubit™ dsDNA HS Assay kit protocol, Agilent™ DNA 1000 kit, or TruSeq™ Sequencing Library Preparation; Low-Throughput (LT) protocol may be used to quantify nucleic acids. Cell-free nucleic acids may be fetal in origin (via fluid taken from a pregnant subject), or may be derived from tissue of the subject itself. Cell-free nucleic acids can be derived from a neoplasm (e.g. a tumor or an adenoma).

Generally, cell-free nucleic acids are extracted and isolated from bodily fluids through a partitioning step in which cell-free nucleic acids, as found in solution, are separated from cells and other non-soluble components of the bodily fluid. Partitioning may include, but is not limited to, techniques such as centrifugation or filtration. In other cases, cells are not partitioned from cell-free nucleic acids first, but rather lysed. In one example, the genomic DNA of intact cells is partitioned through selective precipitation. Cell-free nucleic acids, including DNA, may remain soluble and may be separated from insoluble genomic DNA and extracted. Generally, after addition of buffers and other wash steps specific to different kits, nucleic acids may be precipitated using isopropanol precipitation. Further clean up steps may be used such as silica based columns to remove contaminants or salts. General steps may be optimized for specific applications. Non-specific bulk carrier nucleic acids, for example, may be added throughout the reaction to optimize certain aspects of the procedure such as yield.

Cell-free DNA molecules can be at most 500 nucleotides in length, at most 400 nucleotides in length, at most 300 nucleotides in length, at most 250 nucleotides in length, at most 225 nucleotides in length, at most 200 nucleotides in length, at most 190 nucleotides in length, at most 180 nucleotides in length, at most 170 nucleotides in length, at most 160 nucleotides in length, at most 150 nucleotides in length, at most 140 nucleotides in length, at most 130 nucleotides in length, at most 120 nucleotides in length, at most 110 nucleotides in length, or at most 100 nucleotides in length.

Cell-free DNA molecules can be at least 500 nucleotides in length, at least 400 nucleotides in length, at least 300 nucleotides in length, at least 250 nucleotides in length, at least 225 nucleotides in length, at least 200 nucleotides in length, at least 190 nucleotides in length, at least 180 nucleotides in length, at least 170 nucleotides in length, at least 160 nucleotides in length, at least 150 nucleotides in length, at least 140 nucleotides in length, at least 130 nucleotides in length, at least 120 nucleotides in length, at least 110 nucleotides in length, or at least 100 nucleotides in length. In particular, cell-free nucleic acids can be between 140 and 180 nucleotides in length.

Cell-free DNA can comprise DNA molecules from healthy tissue and tumors in various amounts. Tumor-derived cell-free DNA can be at least 0.1% of the total amount of cell-free DNA in the sample, at least 0.2% of the total amount of cell-free DNA in the sample, at least 0.5% of the total amount of cell-free DNA in the sample, at least 0.7% of the total amount of cell-free DNA in the sample, at least 1% of the total amount of cell-free DNA in the sample, at least 2% of the total amount of cell-free DNA in the sample, at least 3% of the total amount of cell-free DNA in the sample, at least 4% of the total amount of cell-free DNA in the sample, at least 5% of the total amount of cell-free DNA in the sample, at least 10% of the total amount of cell-free DNA in the sample, at least 15% of the total amount of cell-free DNA in the sample, at least 20% of the total amount of cell-free DNA in the sample, at least 25% of the total amount of cell-free DNA in the sample, or at least 30% of the total amount of cell-free DNA in the sample, or more.

In some cases, DNA molecules can be sheared during the extraction process and comprise fragments between 100 and 400 nucleotides in length. In some cases, nucleic acids can be sheared after extraction can comprise nucleotides between 100 and 400 nucleotides in length. In some cases, DNA molecules are already between 100 and 400 nucleotides in length and additional shearing is not purposefully implemented.

A subject can be an animal. A subject can be a mammal, such as a dog, horse, cat, mouse, rat, or human. A subject can be a human. A subject can be suspected of having cancer. A subject can have previously received a cancer diagnosis. The cancer status of a subject may be unknown. A subject can be male or female. A subject can be at least 20 years old, at least 30 years old, at least 40 years old, at least 50 years old, at least 60 years old, or at least 70 years old.

Sequencing may be by any method known in the art. For example, sequencing techniques include classic techniques (e.g., dideoxy sequencing reactions (Sanger method) using labeled terminators or primers and gel separation in slab or capillary) and next generation techniques. Exemplary techniques include sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, SOLiD sequencing targeted sequencing, single molecule real-time sequencing, exon sequencing, electron microscopy-based sequencing, panel sequencing, transistor-mediated sequencing, direct sequencing, random shotgun sequencing, whole-genome sequencing, sequencing by hybridization, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, real-time sequencing, reverse-terminator sequencing, nanopore sequencing, MS-PET sequencing, and a combination thereof. In some embodiments, the sequencing method is massively parallel sequencing, that is, simultaneously (or in rapid succession) sequencing any of at least 100, 1000, 10,000, 100,000, 1 million, 10 million, 100 million, or 1 billion polynucleotide molecules. In some embodiments, sequencing can be performed by a gene analyzer such as, for example, gene analyzers commercially available from Illumina or Applied Biosystems. Sequencing of separated molecules has more recently been demonstrated by sequential or single extension reactions using polymerases or ligases as well as by single or sequential differential hybridizations with libraries of probes. Sequencing may be performed by a DNA sequencer (e.g., a machine designed to perform sequencing reactions). In some embodiments, a DNA sequencer can comprise or be connected to a database, for example, that contains DNA sequence data.

A sequencing technique that can be used includes, for example, use of sequencing-by-synthesis systems. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pubs. 2011/0009278; 2007/0114362; 2006/0292611; 2006/0024681, each of which are incorporated by reference in their entirety.

Another example of a sequencing technology that can be used includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing (Soni & Meller, 2007, Progress toward ultrafast DNA sequence using solid-state nanopores, Clin Chem 53(11):1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope as described, for example, by Moudrianakis, E. N. and Beer M., in Base sequence determination in nucleic acids with the electron microscope, III. Chemistry and microscopy of guanine-labeled DNA, PNAS 53:564-71 (1965). In one example of the technique, individual DNA molecules are labeled using metallic labels that are distinguishable using an electron microscope. These molecules are then stretched on a flat surface and imaged using an electron microscope to measure sequences.

Prior to sequencing, adaptor sequences can be attached to the nucleic acid molecules and the nucleic acids can be enriched for particular sequences of interest. Sequence enrichment can occur before or after the attachment of adaptor sequence.

The nucleic acid molecules or enriched nucleic acid molecules can be attached to any sequencing adaptor suitable for use on any sequencing platform disclosed herein. For example, a sequence adaptor can comprise a flow cell sequence, a sample barcode, or both. In another example, a sequence adaptor can be a hairpin shaped adaptor, a Y-shaped adaptor, a forked adaptor, and/or comprise a sample barcode. In some cases, the adaptor does not comprise a sequencing primer region. In some cases the adaptor-attached DNA molecules are amplified, and the amplification products are enriched for specific sequences as described herein. In some cases, the DNA molecules are enriched for specific sequences after preparing a sequencing library. Adaptors can comprise barcode sequence. The different barcode can be at least 1, 2, 3, 4, 5, 6, 7, 8, 9, 10, 11, 12, 13, 14, 15, 16, 17, 18, 19, 20, 21, 22, 23, 24, 25, or more (or any length as described throughout) nucleic acid bases, e.g., 7 bases. The barcodes can be random sequences, degenerate sequences, semi-degenerate sequences, or defined sequences. In some cases, there is a sufficient diversity of barcodes that substantively (e.g., at least 70%, at least 80%, at least 90%, or at least 99% of) each nucleic acid molecule is tagged with a different barcode sequence. In some cases, there is a sufficient diversity of barcodes that substantively (e.g., at least 70%, at least 80%, at least 90%, or at least 99% of) each nucleic acid molecule from a particular genetic locus is tagged with a different barcode sequence.

A sequencing adaptor can comprise a sequence capable of hybridizing to one or more sequencing primers. A sequencing adaptor can further comprise a sequence hybridizing to a solid support, e.g., a flow cell sequence. For example, a sequencing adaptor can be a flow cell adaptor. The sequencing adaptors can be attached to one or both ends of a polynucleotide fragment. In another example, a sequencing adaptor can be hairpin shaped. For example, the hairpin shaped adaptor can comprise a complementary double-stranded portion and a loop portion, where the double-stranded portion can be attached (e.g., ligated) to a double-stranded polynucleotide. Hairpin shaped sequencing adaptors can be attached to both ends of a polynucleotide fragment to generate a circular molecule, which can be sequenced multiple times.

In some cases, none of the library adaptors contains a sample identification motif (or sample molecular barcode). Such sample identification motif can be provided via sequencing adaptors. A sample identification motif can include a sequencer of at least 4, 5, 6, 7, 8, 9, 10, 20, 30, or 40 nucleotide bases that permits the identification of polynucleotide molecules from a given sample from polynucleotide molecules from other samples. For example, this can permit polynucleotide molecules from two subjects to be sequenced in the same pool and sequence reads for the subjects subsequently identified.

A sequencer motif includes nucleotide sequence(s) needed to couple a library adaptor to a sequencing system and sequence a target polynucleotide coupled to the library adaptor. The sequencer motif can include a sequence that is complementary to a flow cell sequence and a sequence (sequencing initiation sequence) that can be selectively hybridized to a primer (or priming sequence) for use in sequencing. For example, such sequencing initiation sequence can be complementary to a primer that is employed for use in sequence by synthesis (e.g., Illumina). Such primer can be included in a sequencing adaptor. A sequencing initiation sequence can be a primer hybridization site.

In some cases, none of the library adaptors contains a complete sequencer motif. The library adaptors can contain partial or no sequencer motifs. In some cases, the library adaptors include a sequencing initiation sequence. The library adaptors can include a sequencing initiation sequence but no flow cell sequence. The sequence initiation sequence can be complementary to a primer for sequencing. The primer can be a sequence specific primer or a universal primer. Such sequencing initiation sequences may be situated on single-stranded portions of the library adaptors. As an alternative, such sequencing initiation sequences may be priming sites (e.g., kinks or nicks) to permit a polymerase to couple to the library adaptors during sequencing.

Adaptors can be attached to DNA molecules by ligation. In some cases, the adaptors are ligated to duplex DNA molecules such that each adaptor differently tags complementary strands of the DNA molecule. In some cases, adaptor sequences can be attached by PCR, wherein a first portion of a single-stranded DNA is complementary to a target sequence and a second portion comprises the adaptor sequence.

Enrichment for particular sequences of interest can be performed by sequence capture methods. Sequence capture can be performed using immobilized probes that hybridize to the targets of interest. Sequence capture can be performed using probes attached to functional groups, e.g., biotin, that allow probes hybridized to specific sequences to be enriched for from a sample by pulldown. In some cases, prior to hybridization to functionalized probes, specific sequences such as adaptor sequences from library fragments can be masked by annealing complementary, non-functionalized polynucleotide sequences to the fragments in order to reduce non-specific or off-target binding. Sequence probes can target specific genes. Sequence capture probes can target specific genetic loci or genes. Such genes can be oncogenes. Exemplary genes targeted by capture probes include those shown in FIG. 1. Exemplary genes with point mutations (SNVs) include, but are not limited to, AKT1, ATM, CCNE1, CTNNB1, FGFR1, GNAS, JAK3, MLH1, NPM1, PTPN11, RIT1, TERT, ALK, BRAF, CDH1, EGFR, FGFR2, HNF1A, KIT MPL, NRAS, RAF1, ROS1, TP53, APC, BRCA1, CDK4, ERBB2, FGFR3, HRAS, KRAS, MYC, NTRK1, R131, SMAD4, TSC1, AR, BRCA2, CDK6, ESR1, GATA3, IDH2, MAP2K2, NFE2L2, PIK3CA, RHEB, SRC, ARID1A, CCND2, CDKN2B, FBXW7, GNAQ, JAK2, MET, NOTCH1, PTEN, RHOA, and STK11. Exemplary genes with copy number variations include, but are not limited to, AR, CCNE1, CDK6, ERBB2, FGFR2, KRAS, MYC, PIK3CA, BRAF, CDK4, EGFR, FGFR1, KIT, MET, PDGFRA, and RAF1. Exemplary genes with gene fusions include, but are not limited to: ALK, FGFR2, FGFR3, NTRK1, RET, and ROS1. Exemplary genes with indels include, but are not limited to: EGFR (for example, at exons 19 and 20), ERBB2 (for example, at exons 19 and 20), and MET (for example, skipping exon 14). Exemplary targets can include CCND1 and CCND2. Sequence capture probes can tile across a gene (e.g., probes can target overlapping regions). Sequence probes can target non-overlapping regions. Sequence probes can be optimized for length, melting temperature, and secondary structure.

Quantitative Measures of Guanine-Cytosine (GC) Content

Guanine-cytosine content is the percentage of nitrogenous bases of a DNA molecule that are either guanine or cytosine. A quantitative measure related to GC content for a genetic locus can be the GC content of the entire genetic locus. A quantitative measure related to GC content for a genetic locus can be the GC content of the exonic regions of the gene. A quantitative measure related to GC content for a genetic locus can be the GC content of the regions covered by reads mapping to the genetic locus. A quantitative measure related to GC content can be the GC content of the sequence capture probes corresponding to the genetic locus. A quantitative measure related to GC content for a genetic locus can be a measure related to central tendency of the GC content of the sequence capture probes corresponding to the genetic locus. The measure related to central tendency can be any measure of central tendency such as mean, median, or mode. The measure related to central tendency can be the median. GC content of a given region can be measured by dividing the number of guanosine and cytosine bases by the total number of bases over that region.

Quantitative Measures of Sequencing Read Coverage

A quantitative measure related to sequencing read coverage is a measure indicative of the number of reads derived from a DNA molecule corresponding to a genetic locus (e.g., a particular position, base, region, gene or chromosome from a reference genome). In order to associate reads to a genetic locus, the reads can be mapped or aligned to the reference. Software to perform mapping or aligning (e.g., Bowtie, BWA, mrsFAST, BLAST, BLAT) can associate a sequencing read with a genetic locus. During the mapping process, particular parameters can be optimized. Non-limiting examples of optimization of the mapping processing can include masking repetitive regions; employing mapping quality (e.g., MAPQ) score cut-offs; using different seed lengths to generate alignments; and limiting the edit distance between positions of the genome.

Quantitative measures associated with sequencing read coverage can include counts of reads associated with a genetic locus. In some cases, the counts are transformed into new metrics to mitigate the effects of differing sequencing depth, library complexity, or size of the genetic locus. Exemplary metrics are Read Per Kilobase per Million (RPKM), Fragments Per Kilobase per Million (FPKM), Trimmed Mean of M values (TMM), variance stabilized raw counts, and log transformed raw counts. Other transformations are also known to those of skill in the art that may be used for particular applications.

Quantitative measures can be determined using collapsed reads, wherein each collapsed read corresponds to an initial template DNA molecule. Methods to collapse and quantify read families are found in PCT/US2013/058061 and PCT/US2014/000048, each of which is herein incorporated by reference in its entirety. In particular, collapsing methods can be employed that use barcodes and sequence information from the sequencing read to collapse reads into families, such that each family shares barcode sequences and at least a portion of the sequencing read sequence. Each family is then, for the majority of the families, derived from a single initial template DNA molecule. Counts derived from mapping sequences from families can be referred to as "unique molecular counts" (UMCs). In some cases, determining a quantitative measure related to sequencing read coverage comprises normalizing UMCs by a metric related to library size to provide normalized UMCs ("normalized UMCs"). Exemplary methods are dividing the UMC of a genetic locus by the sum of all UMCs; dividing the UMC of a genetic locus by the sum of all autosomal UMCs. When comparing multiple sequencing read data sets, UMCs can, for example, be normalized by the median UMCs of the genetic loci of the two sequencing read data sets. In some cases, the quantitative measure related to sequencing read coverage can be normalized UMCs that are further normalized as follows: (i) normalized UMCs are determined for corresponding genetic loci from sequencing reads derived from training samples; (ii) for each genetic locus, normalized UMCs of the sample are normalized by the median of the normalized UMCs of the training samples at the corresponding loci, thereby providing Relative Abundances (RAs) of genetic loci.

Consensus sequences can identified based on their sequences, for example by collapsing sequencing reads based on identical sequences within the first 5, 10, 15, 20, or 25 bases. In some cases, collapsing allows for 1 difference, 2 differences, 3 differences, 4 differences, or 5 differences in the reads that are otherwise identical. In some cases, collapsing uses the mapping position of the read, for example the mapping position of the initial base of the sequencing read. In some cases, collapsing uses barcodes, and sequencing reads that share barcode sequences are collapsed into a consensus sequence. In some cases, collapsing uses both barcodes and the sequence of the initial template molecules. For example, all reads that share a barcode and map to the same position in the reference genome can be collapsed. In another example, all reads that share a barcode and a sequence of the initial template molecule (or a percentage identity to a sequence of the initial template molecule) can be collapsed.

In some cases, quantitative measures of sequencing read coverage are determined for specific sub-regions of a genome. Regions can be bins, genes of interest, exons, regions corresponding to sequence probes, regions corresponding to primer amplification products, or regions corresponding to primer binding sites. In some cases, sub-regions of the genome are regions corresponding to sequence capture probes. A read can map to a region corresponding to the sequence capture probe if at least a portion of the read maps at least a portion of the region corresponding to the sequence capture probe. A read can map to a region corresponding to the sequence capture probe if at least a portion of the read maps to the majority of the region corresponding to the sequence capture probe. A read can map to a region corresponding to the sequence capture probe if at least a portion of the read maps across the center point of the region corresponding to the sequence capture probe. In some cases, a quantitative measure related to sequencing read coverage of a genetic locus is the median of the RAs of the probes corresponding to genomic locations within the genetic locus. For example, if KRAS is covered by three probes, which have RAs of 2, 3, and 5, the RA of the genetic locus would be 3.

"Saturation Equilibrium" Correction

In general, the methods described herein can be used to increase the specificity and sensitivity of variant calling (e.g., detecting copy number variants) in a nucleic acid sample. For example, the methods can decrease the amount of noise or distortion in a data sample, reducing the number of false positive variants detected. As noise and/or distortion decrease, specificity and sensitivity increase. Noise can be thought of as an unwanted random addition to a signal. Distortion can be thought of as an alteration in the amplitude of a signal or portion of a signal.

Noise can be introduced through errors in copying and/or reading a polynucleotide. For example, in a sequencing process, a single polynucleotide can first be subject to amplification. Amplification can introduce errors, so that a subset of the amplified polynucleotides may contain, at a particular locus, a base that is not the same as the original base at that locus. Furthermore, in the reading process a base at any particular locus may be read incorrectly. As a consequence, the collection of sequence reads can include a certain percentage of base calls at a locus that are not the same as the original base. In typical sequencing technologies this error rate can be in the single digits, e.g., 2%-3%. When a collection of molecules that are all presumed to have the same sequence are sequenced, this noise is sufficiently small that one can identify the original base with high reliability.

However, if a collection of parent polynucleotides includes a subset of polynucleotides having sequence variants at a particular locus, noise can be a significant problem. This can be the case, for example, when cell free DNA includes not only germline DNA, but DNA from another source, such as fetal DNA or DNA from a cancer cell. In this case, if the frequency of molecules with sequence variants is in the same range as the frequency of errors introduced by the sequencing process, then true sequence variants may not be distinguishable from noise. This could interfere, for example, with detecting sequence variants in a sample.

Distortion can be manifested in the sequencing process as a difference in signal strength, e.g., total number of sequence reads, produced by molecules in a parent population at the same frequency. Distortion can be introduced, for example, through amplification bias, GC bias, or sequencing bias. This could interfere with detecting copy number variation in a sample. GC bias results in the uneven representation of areas rich or poor in GC content in the sequence reading.

Methods disclosed herein comprise determining an initial set of genetic loci for use in determining a baseline by removing from a data set those genetic loci for which the quantitative measure related to sequencing read coverage or the transformed quantitative measure related to sequencing read coverage differs most from a predictive model (which can be referred to herein as removing high-variance genetic loci), thereby providing a first set of remaining genetic loci. In some instances, removing these genetic loci comprises fitting a model that relates the quantitative measures related to sequencing read coverage to the quantitative measures related to GC content of the genetic loci. For example, the predictive model can relate the RAs of the genetic loci to the GC content of the loci. In some cases, the predictive model is a regression model, including non-parametric regression models such as LOESS and LOWESS regression models. In some cases, baselining is performed by removing 5%, 10%, 15%, 20%, 25%, 30%, 35%, 40%, 45%, 50%, 55%, 60%, 65%, or 70% of the genetic loci that deviate the most from the predictive model. In some cases, baselining is performed by removing at least 5%, at least 10%, at least 15%, at least 20%, at least 25%, at least 30%, at least 35%, at least 40%, at least 45%, at least 50%, at least 55%, at least 60%, at least 65%, or at least 70% of the genetic loci that deviate the most from the predictive model. In some cases, deviation is determined by measuring the residuals of the genetic loci relative to the model. The exact cut-off can be chosen to provide exclude a specific amount of variance from the remaining genetic loci.

Methods to determine a quantitative measure related to the probability that a strand of DNA from the sample derived from the genetic locus is represented within the sequencing reads are disclosed in PCT/US2014/072383, which is hereby incorporated by reference in its entirety. Determining the quantitative measure can comprise estimating number of initial template DNA molecules derived from a locus that were present in the sample. The probability that a double strand polynucleotide generates no sequence reads can be determined based on the relative number of reads representing both strands of an initial template DNA molecule and reads representing only a single strand of an initial template DNA molecule.

The number of undetected initial template DNA molecules in a sample can be estimated based on the relative number of reads representing both strands of an initial template DNA molecule and reads representing only a single strand of an initial template DNA molecule. As an example, counts for a particular genetic locus, Locus A, are recorded, where 1000 molecules are paired (e.g., both strands are detected) and 1000 molecules are unpaired (e.g., only a single strand is detected). It should be noted that the terms "paired" and "unpaired" as used herein are distinct from these terms as sometimes applied to sequencing reads to indicated whether both ends or a single-end of a molecule are sequenced. Assuming a uniform probability, p, for an individual Watson or Crick strand to make it through the process subsequent to conversion, one can calculate the proportion of molecules that fail to make it through the process (Unseen) as follows: R, the ratio of paired to unpaired molecules=1000/1000=1, therefore $R=1-p^2/(2p(1-p))$. This implies that $p=2/3$ and that the quantity of lost molecules is equal to $(1-p)^2=1/9$. Thus in this example, approximately 11% of converted molecules are lost and never detected. In addition to using binomial distribution, other methods of estimating numbers of unseen molecules include exponential, beta, gamma or empirical distributions based on the redundancy of sequence reads observed. In the latter case, the distribution of read counts for paired and unpaired molecules can be derived from such redundancy to infer the underlying distribution of original polynucleotide molecules at a particular locus. This can often lead to a better estimation of the number of unseen molecules. In some cases, p is the quantitative measure related to the probability that a strand of DNA from the sample derived from the genetic locus is represented in the sequencing reads. In some cases, p is similarly derived, but a different model of read distribution is used (e.g., binomial, poisson, beta, gamma, and negative binomial distribution).

A transformation for the quantitative measure related to sequencing read coverage can be determined by relating the quantitative measure or transformed sequencing read coverage from a set of genetic loci with high-variance genetic loci removed to the quantitative measure related to GC content and the quantitative measure related to the probability that a strand of DNA derived from the genetic locus is represented within the sequencing reads. In some cases, the remaining genetic loci are assumed to be diploid and/or to be present at the same copy number. In some instances, a transformation is determined by fitting a measure related to central tendency of the quantitative measures related to sequencing read coverage of the remaining genetic loci by the quantitative measure related to GC content and the quantitative measure related to the probability that a strand of DNA derived from the genetic locus is represented within the sequencing reads. A transformation can, for example, (i) fit the central tendency of the quantitative measures sequencing read coverage of the remaining genetic loci after removal of high-variance genetic loci by both the quantitative measures related to GC content and the quantitative measures related to the probability that a strand of DNA derived from the genetic locus is represented within the sequencing reads. In some instances, the measure related to central tendency of the quantitative measures of sequencing read coverage of the remaining loci is the central tendency of the UMCs of the remaining genetic loci. In some instances, a surface approximation is used to fit a surface of UMCs of the remaining genetic loci or the central tendency of the UMCs of the remaining genetic loci by (i) the quantitative measures related to GC content and (ii) the quantitative measures related to the probability that a strand of DNA derived from the genetic locus is represented within the sequencing reads. For example, the surface approximation can be a two-dimensional second-degree polynomial surface fit of the measure related to initial template DNA molecules (e.g., UMCs) by the quantitative measures of GC content and p. In some cases, the transformed quantitative measure related to sequencing coverage is the value expected based on the transformation determined above calculated from (i) the quantitative measures related to GC content and (ii) the quantitative measures related to the probability that a strand of DNA derived from the genetic locus is represented within the sequencing reads. In some cases, the transformed quantitative measure related to sequencing coverage is the residual of each genetic locus (e.g., the difference or quotient of the expected quantitative measure related to sequencing read coverage of a locus based on the surface approximation and the observed quantitative measure related to sequencing read coverage of the genetic locus in the sample). Optionally, after the transformed quantitative measure related to sequencing coverage is determined, high-variance genetic loci can again be removed as described above based on the new transformed quantitative measures of sequencing read coverage.

"Probe Efficiency" Correction

Disclosed herein are methods to determine and remove biases for genetic loci using reference samples. In some cases, the reference samples are sequencing reads from cell-free DNA from subjects without cancer. In some cases, the reference samples are sequencing reads from cell-free DNA from subjects with cancer cells that substantially lack copy number variation in the genetic loci of interest. In some cases, the reference samples are sequencing reads from cell-free DNA from subjects with cancer, where regions suspected of have undergone copy number variation are excluded from analysis. In some cases, the reference sample is a plasma sample from a subject without cancer. In some cases, the reference sample is a plasma sample from a subject with cancer.

Each of the genetic loci of the reference samples can be processed as described above in "saturation equilibrium correction" to provide transformed quantitative measures of sequencing read coverage. In some cases, the transformed quantitative measure related to sequencing coverage is the value expected based on the transformation determined above calculated from (i) the quantitative measures related to GC content and (ii) the quantitative measures related to the probability that a strand of DNA derived from the genetic locus from the reference genetic loci is represented within the sequencing reads. In some cases, the transformed quantitative measure related to sequencing coverage is the residual of each reference genetic locus (e.g., the difference or quotient of the expected quantitative measure related to sequencing read coverage of a locus based on the surface approximation and the observed quantitative measure related to sequencing read coverage of the genetic locus in the reference sample). The transformed quantitative measure related to sequencing read coverage of the genetic locus in the reference sample can be thought of as the "efficiency" of the genetic locus. For example, a genetic locus that is inefficiently amplified will have a lower UMC than a genetic locus (present at the same copy number in the sample) that is very efficiently amplified.

The transformed quantitative measure related to sequencing read coverage of the sample can be corrected based on the determined efficiency of the genetic loci from the reference sample(s). This correction can reduce variance introduced into the sample by the process of producing the sequencing reads from the sample, which can be related to ligation efficiency, pulldown efficiency, PCR efficiency, flow cell clustering loss, demultiplexing loss, collapsing loss, and alignment loss. In one embodiment, correction comprises dividing or subtracting the post-saturation transformed quantitative measures of sequencing coverage of the sample by the predicted post-saturation transformed quantitative measure related to sequencing coverage. In some instances, the predicted post-saturation transformed quantitative measure related to sequencing coverage of the genetic loci is determined by fitting a relationship between the post-saturation transformed quantitative measure related to sequencing coverage of the genetic loci from the sample and the post-saturation transformed quantitative measure related to sequencing read coverage of the references. In some cases, fitting comprises performing local regression (e.g., LOESS or LOWESS) or robust linear regression of the post-saturation transformed quantitative measure related to sequencing coverage of the genetic loci from the sample on the post-saturation transformed quantitative measure related to sequencing read coverage of the references. In some cases, the fitting can be linear regression, non-linear regression, or non-parametric regression.

Optionally, the transformed quantitative measure from the probe efficiency correction can be the input into the "saturation equilibrium correction" transformation to produce a third, further transformed quantitative measure related to sequencing read coverage with reduced variance. In general, transformed quantitative measures of sequencing coverage can be transformed using any of the methods disclosed herein additional times in order to further reduce the variance within the transformed quantitative measures of sequencing read coverage.

Gene Level Summaries

Gene level summaries of inferred copy number can be determined based on the transformed quantitative measures of sequencing read coverage determined as disclosed herein. Copy number can be inferred relative to the baseline selected in the above operations by discarding high variance genetic loci. For example, if the remaining genetic loci are inferred to be diploid in the sample, then genetic loci for which the transformed quantitative measure related to sequencing coverage differ from the baseline can be inferred to have undergone copy number alteration in the tumor cells. In some instances, gene-level z-scores are calculated using observed gene-level median of probe signal and estimated standard deviation calculated using observed probe-level standard deviation estimate in a gene and whole-genome normal diploid probe signal standard deviation.

Minor-Allele Frequency Baseline Optimization

Provided herein are methods to detect errors and correct errors in gene level summaries of copy number described herein using minor allele frequencies of variants in the sequencing reads. Sequence variants present in between 10% and 90%, between 20% and 80%, between 30% and 70%, between 40% and 60%, or approximately 50% of sequencing reads from nucleic acids from a cell-free bodily fluid can be heterozygous variants present in the germline sequence of the subject. In some instances, genetic loci have been determined to have undergone amplification as described above. The quantities of variants are compared to the inferred copy number to determine if variant frequency is inconsistent with the inferred copy number. In one example, heterozygous genetic loci can be examined in the genetic loci that were used to determine the baseline copy number (e.g., the genetic loci remaining after exclusion of the high-variance genetic loci). In some cases, numerous genetic loci in the sample have been amplified, and this baseline can be misidentified. In such cases, heterozygosity may deviate from a 1:1 ratio, and the inaccurate baselining is detected and corrected. In a second example, example, a genetic locus can be inferred to be present at a triploid copy number based on the transformed quantitative measure related to sequencing read coverage. If the germline genome of the subject has one chromosome with a first allele of the genetic locus and a second chromosome had a second allele, then the first or second allele may have duplicated in the cancer cells.

Langmuir-Like Saturation Model

Without being bound by theory, disclosed herein is a Langmuir-like saturation model assumed to be the governing mechanism of bait-cfDNA interactions based on exploration of historical clinical data as well as targeted experiments involving synthetic spike-in model systems. Hence, in the absence of interfering assay effects (e.g. ligation efficiencies, PCR amplification biases, sequencing artifacts, etc), bait pulldown process may be described as $$\text{Unique molecule count} = I_{sat} \frac{K \cdot CopyNumber}{1 + K \cdot CopyNumber}$$

Figure 8:
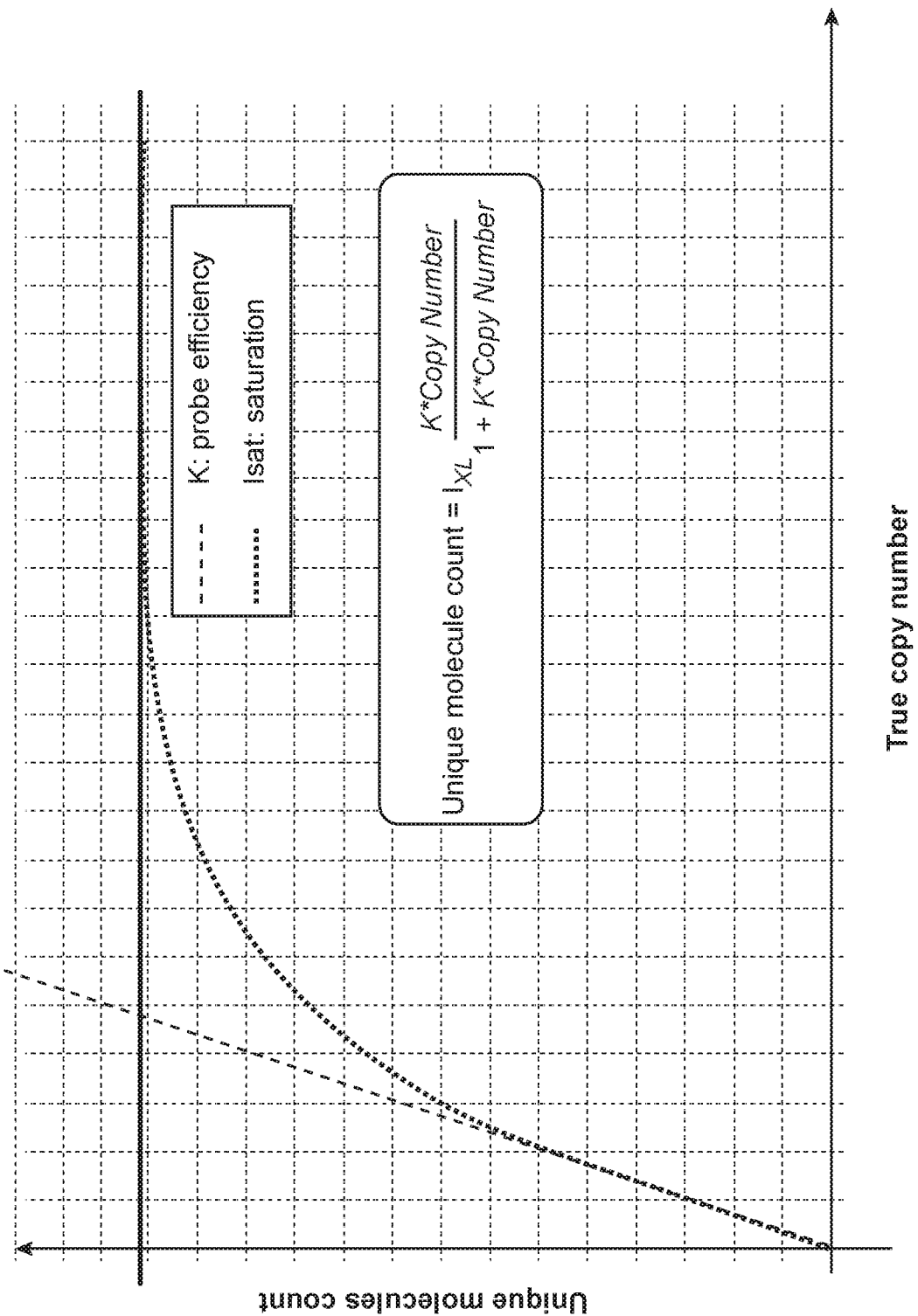
FIG. 8 illustrates a proposed Langmuir model of interactions between true copy number and unique molecular counts related to probe saturation and probe efficiency.

K in this description is bait efficiency, which is dependent on bait sequence characteristics and its interactions with DNA fragments in genomic vicinity of the targeted bait location. $I_{sat}$ is a saturation parameter driven by the limited initial bait count in the pulldown reaction, which is a function of total bait pool concentration as well as replication count. Replication count as used herein refers to the relative or absolute amount of sequence capture probe present. For example, sequence capture arrays can provide for different molar quantities of probes on an array to account for differing probe efficiencies. FIG. 8 illustrates the model relating true copy number and unique molecule count based on bait efficiency, K, and saturation parameter $I_{sat}$.

Bait efficiency K is largely driven by GC content, while $I_{sat}$ is driven by more complex bait exhaustion mechanisms and RNA secondary structure interactions that can be crudely examined by studying unique molecule count vs. total read count interactions. Aside from non-linear pulldown reactions, probe signal can be further modeled by a multiplicative model involving the following assumption: under a naive model cfDNA fragments are uniformly distributed by genomic position with stochastic sampling process being the dominating factor contributing to coverage variation. Then, copy number signal (e.g., UMCs) can be modeled by relating the observed UMC to the true molecular count in the sample, taking into account the effects the underlying positional cfDNA profile, ligation efficiency, pulldown efficiency, PCR efficiency, flowcell clustering loss, demultiplexing loss, collapsing loss, and alignment loss.

Aside from non-linear pulldown reaction, probe signal can be further modeled by simple multiplicative model, involving the following assumptions. Under a naïve model cfDNA fragments are uniformly distributed by genomic position with stochastic sampling process being the dominating factor contributing to coverage variation. Then, copy number signal, i.e. read count associated with a given probe can be modeled as:

Observed UMC=True UMC×Underlying positional cfDNA profile (bait, cfDNAfragment)×Ligation efficiency (position, size, cfDNAfragment)×pulldown efficiency (probe, cfDNAfragment)×PCR efficiency (DNA fragment)× flow cell clustering loss×demultiplexing loss and collapsing loss×alignment loss (cfDNAfragment sequence).

This model assumes a multiplicative nature of the above model. The underlying bait-specific copy number signal can be inferred from observed UMC (e.g., UMC of a given sequence capture probe) in relation to an established baseline by a series of steps, such as the baseline determination methods disclosed herein.

Methods disclosed herein provide approaches for estimating probe efficiency and bait saturation from the sample and training sets. Alternately, such parameters may be inferred by performing a set of bait titration experiments, where the effect of varying target sequence concentration on UMCs is observed for each probe. If K, $I_{sat}$, and UMC are known, it is then possible to determine a UMC value or range corresponding to tumor cells that have not undergone copy number variation. For example, under the assumption that most of the genetic loci have not undergone copy number alteration, the observed UMCs will largely be derived from diploid samples. Samples that have undergone copy number variation will be those genetic loci for which the UMCs fall outside the expected range for probes with their corresponding values of K and $I_{sat}$. In some cases, for example, the UMC value or range will be a function depending on K and $I_{sat}$ for each probe. For example, the UMC corresponding to a diploid copy number can be different between two probes.

Computer Control Systems

Figure 12:
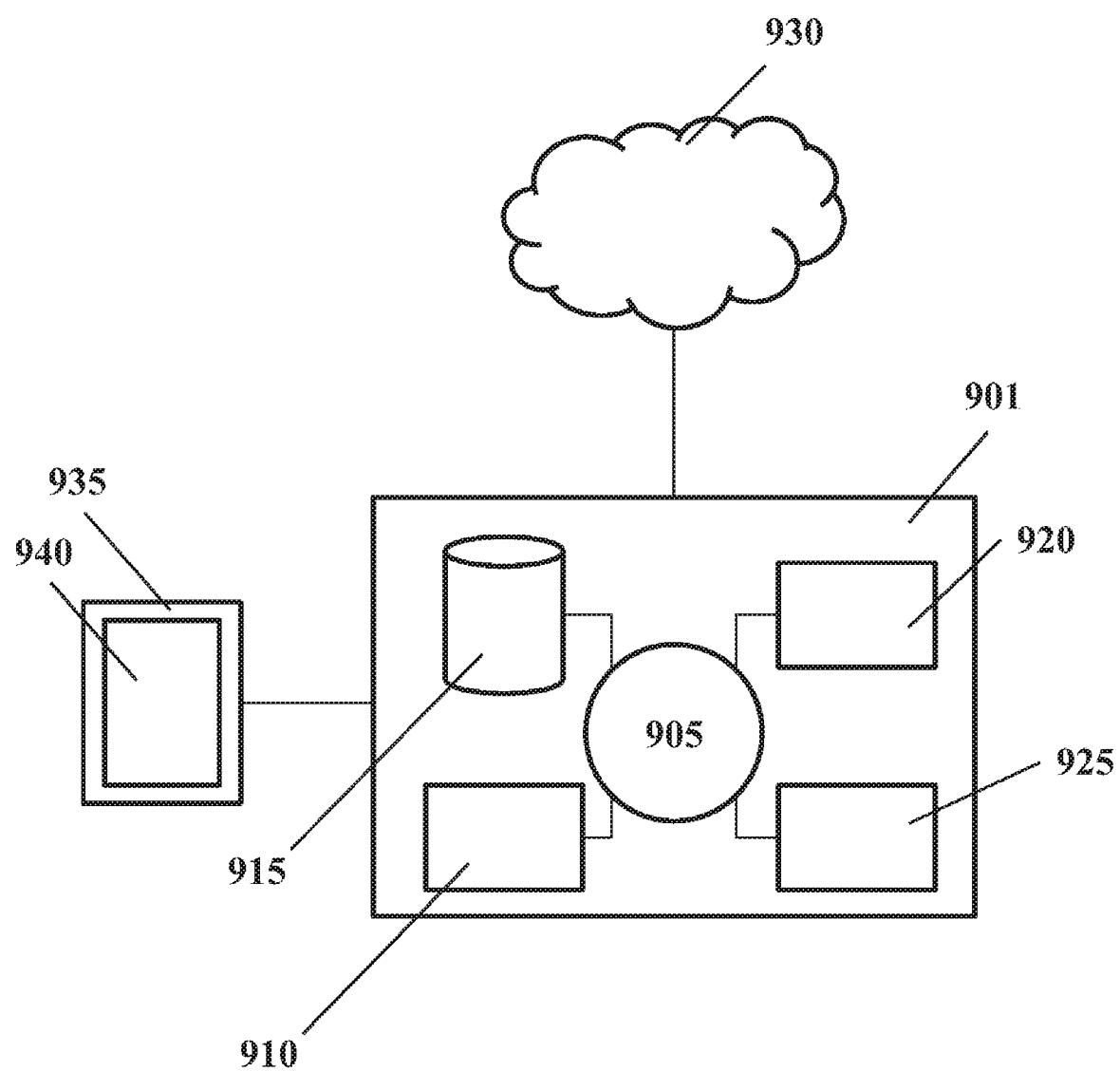
FIG. 12 illustrates a computer system 1201 that is programmed or otherwise configured to implement methods of the present disclosure.

The present disclosure provides computer control systems that are programmed to implement methods of the disclosure. FIG. 12 shows a computer system 1201 that is programmed or otherwise configured to implement methods of the present disclosure. The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include a local area network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, a report. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1205.

EXAMPLES

Example 1

Figure 3:
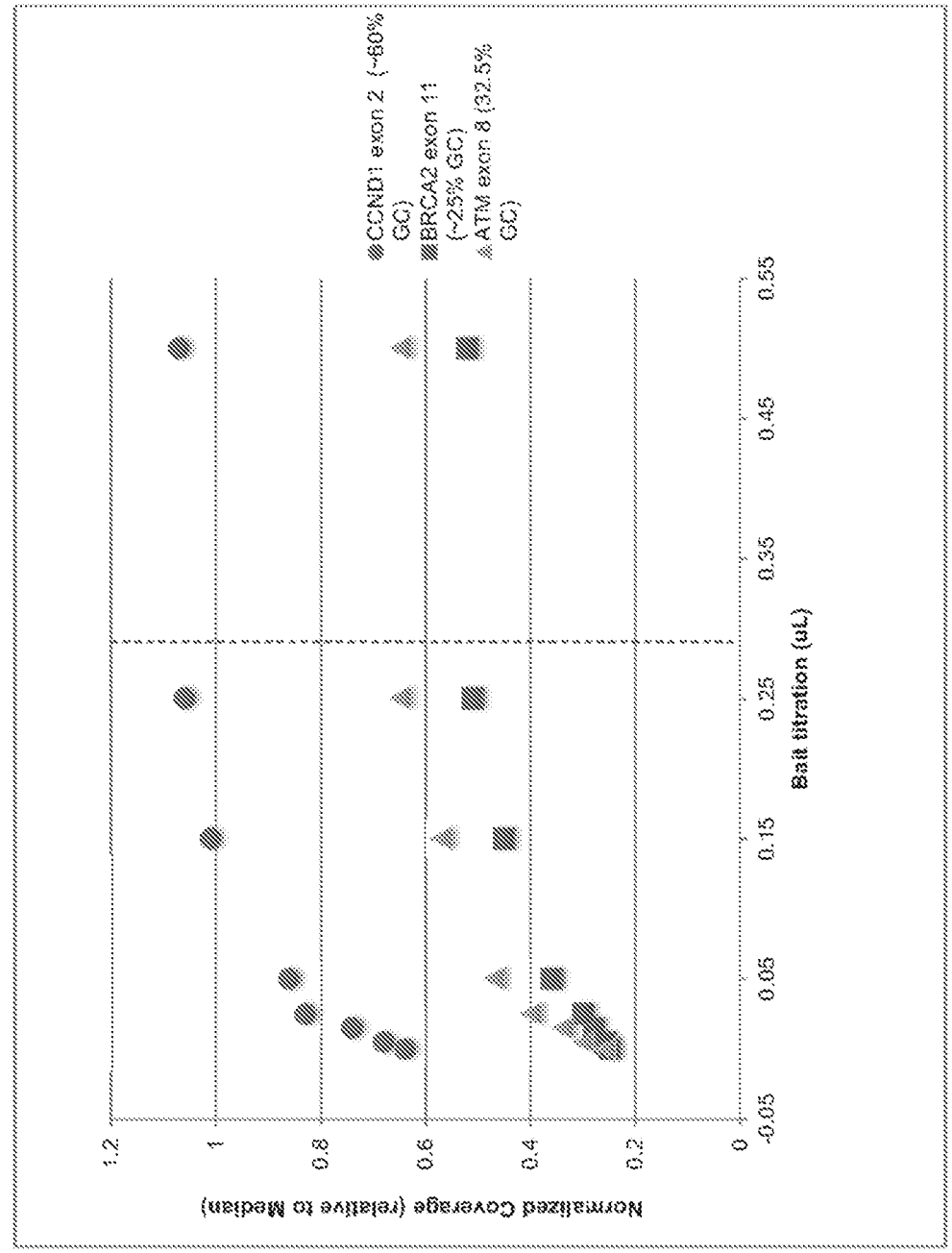
FIG. 3 illustrates a bait optimization experiment relating bait amount with unique molecular counts.

Examination of previously-generated copy number variation spike-in data revealed significant probe-to-probe signal variation, both in raw read counts and UMCs, as well as the probe/gene-level copy number signal response to underlying copy number changes. See FIG. 2. FIG. 3 illustrates the inferred versus theoretical copy number of three genes (CCND1, CCND2, and ERBB2), demonstrating the non-linear response of normalized coverage to the amount of bait in the sample. These results suggest bait depletion during pulldown, which was confirmed by following bait titration effect in neighboring probes within the same gene with sizable differences in unique molecule count (thereby observing faster unique molecule count saturation for probes with high initial UMC).

Figure 4A:
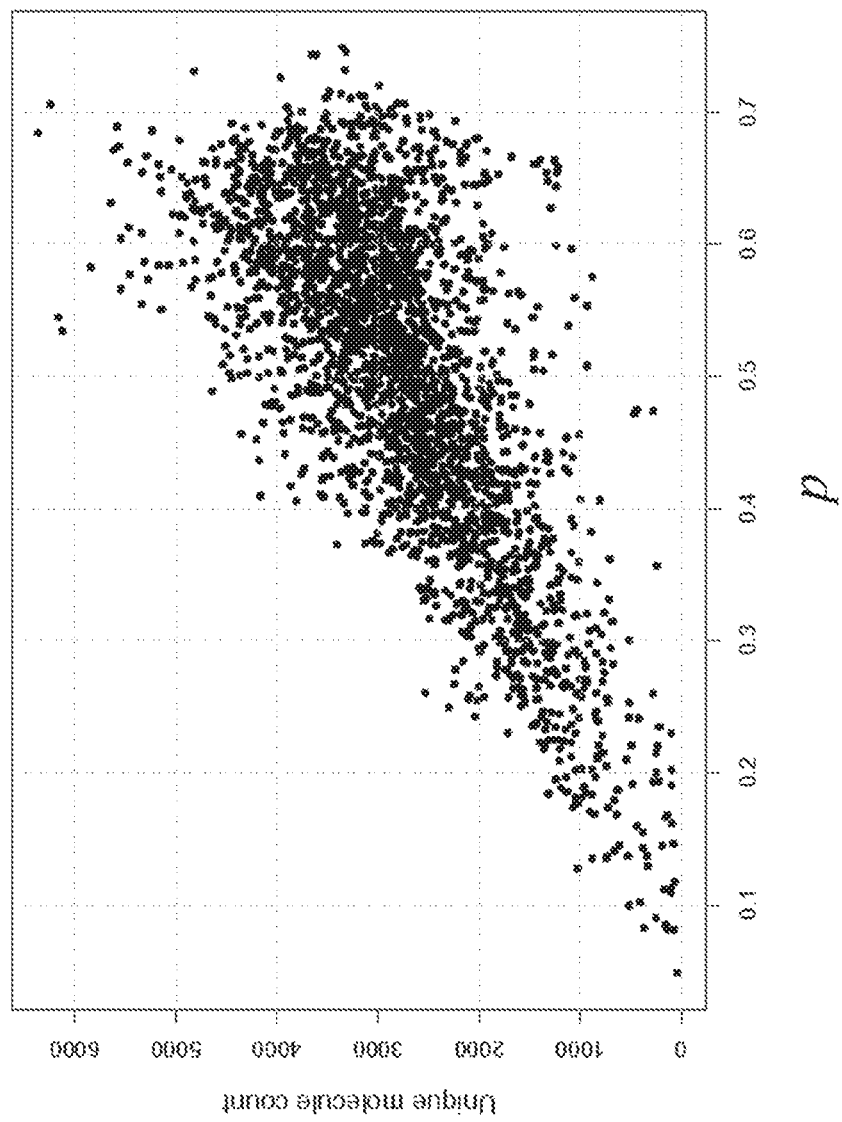
FIG. 4A and FIG. 4B illustrate the nonlinear effects of p (FIG. 4A) and GC content (FIG. 4B) on unique molecular counts.
Figure 4B:
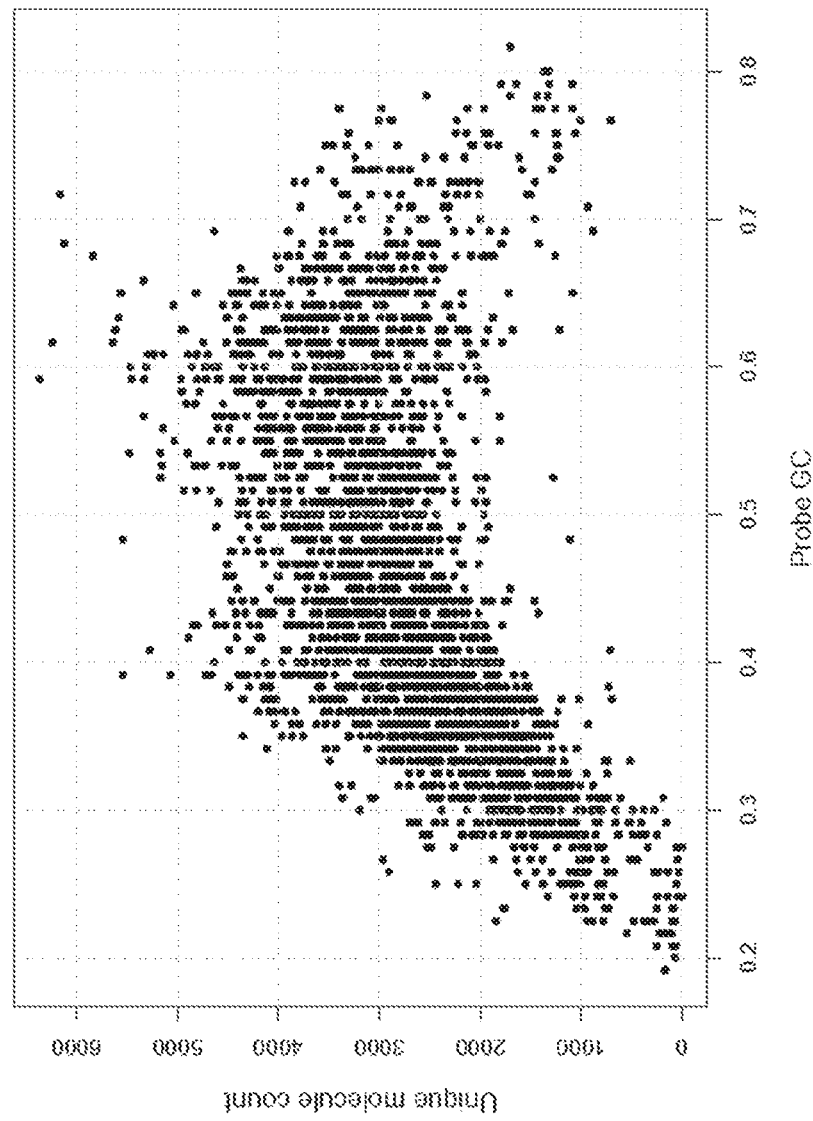

FIG. 4A illustrates that the UMCs associated with each probe has a non-linear response with respect to probe p. FIG. 4B illustrates that UMCs associated with each probe have a non-linear response with respect to probe GC content.

Figure 5:
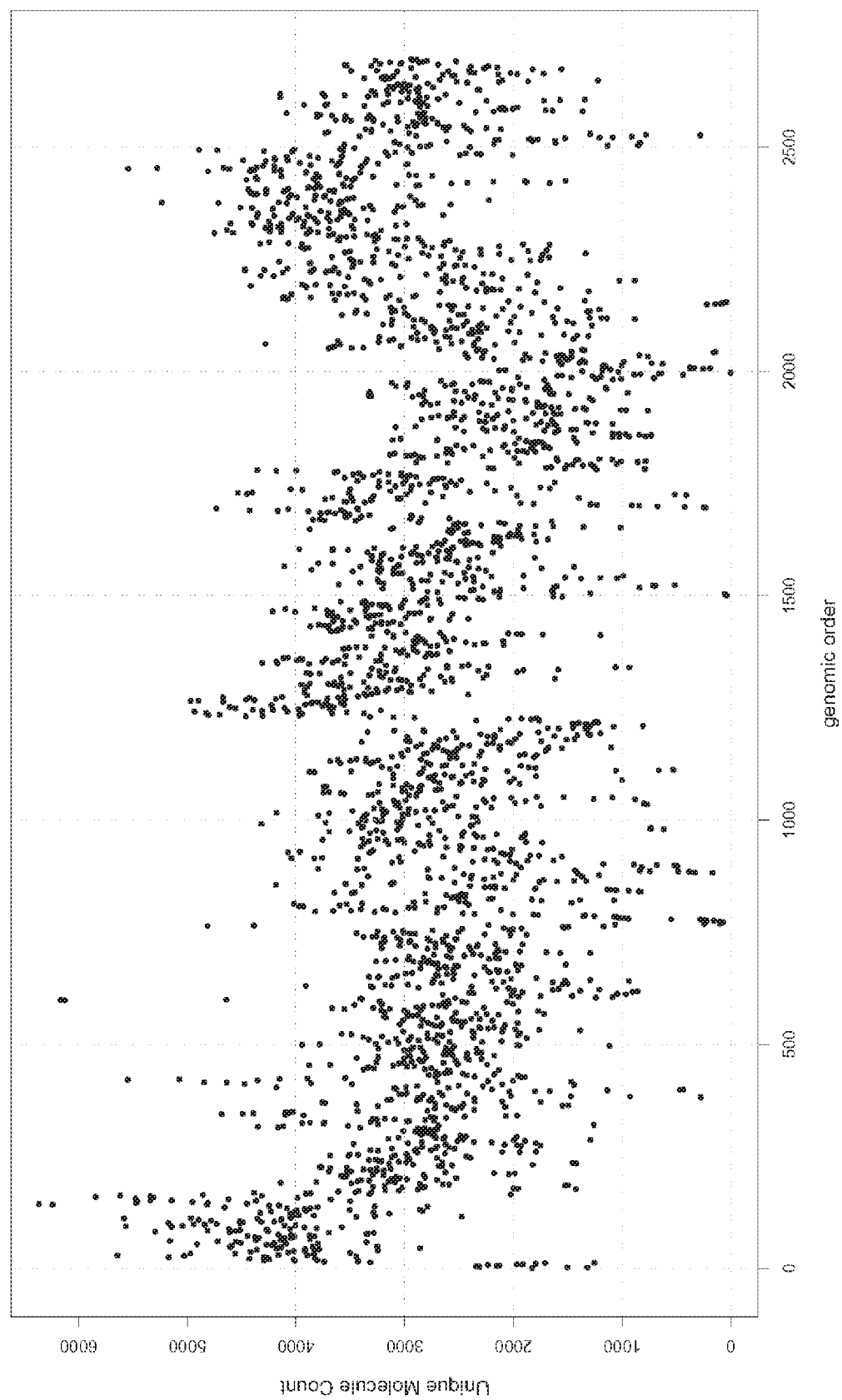
FIG. 5 illustrates unique molecular counts per probe without saturation or probe-efficiency correction being performed.
Figure 6:
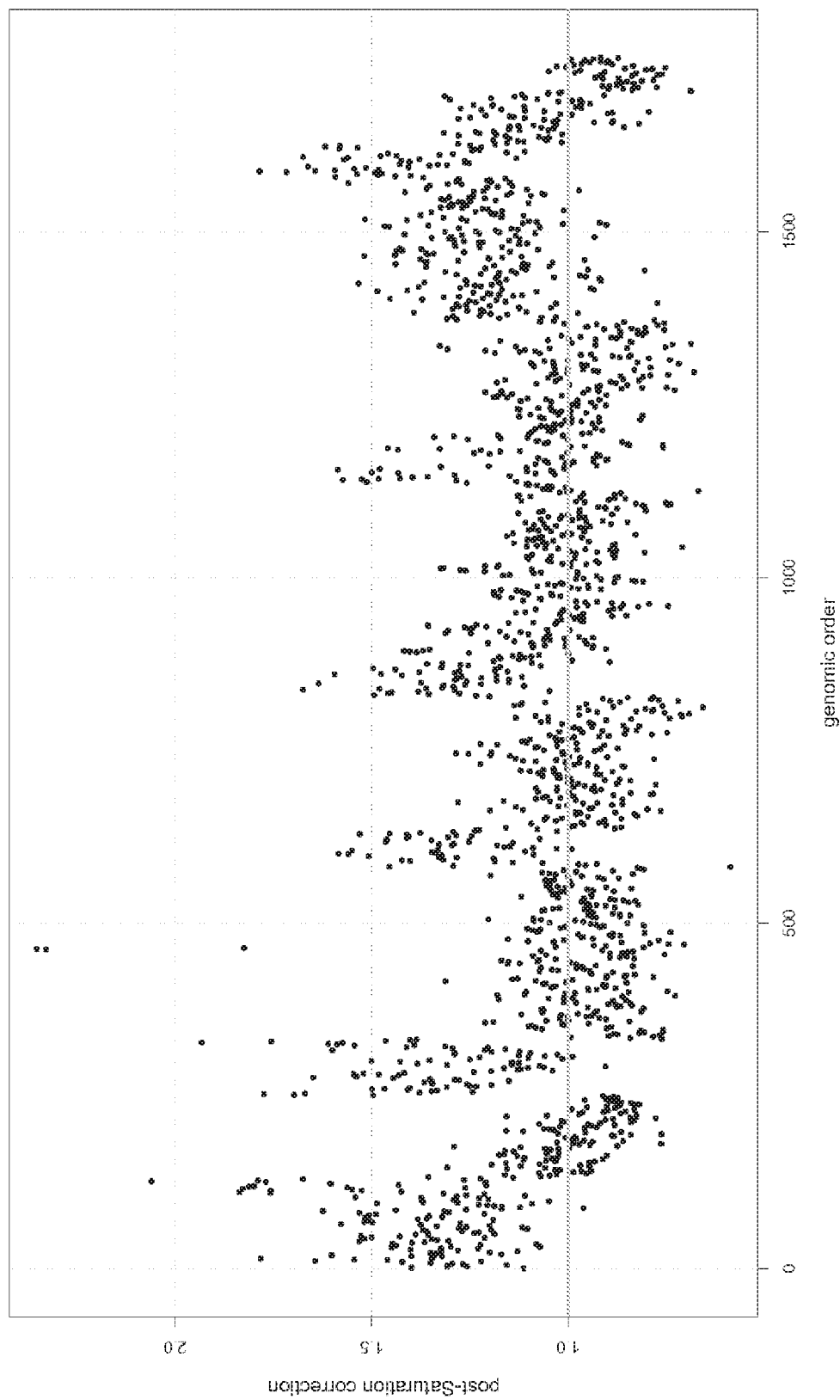
FIG. 6 illustrates post-saturation correction unique molecular counts per probe.
Figure 7:
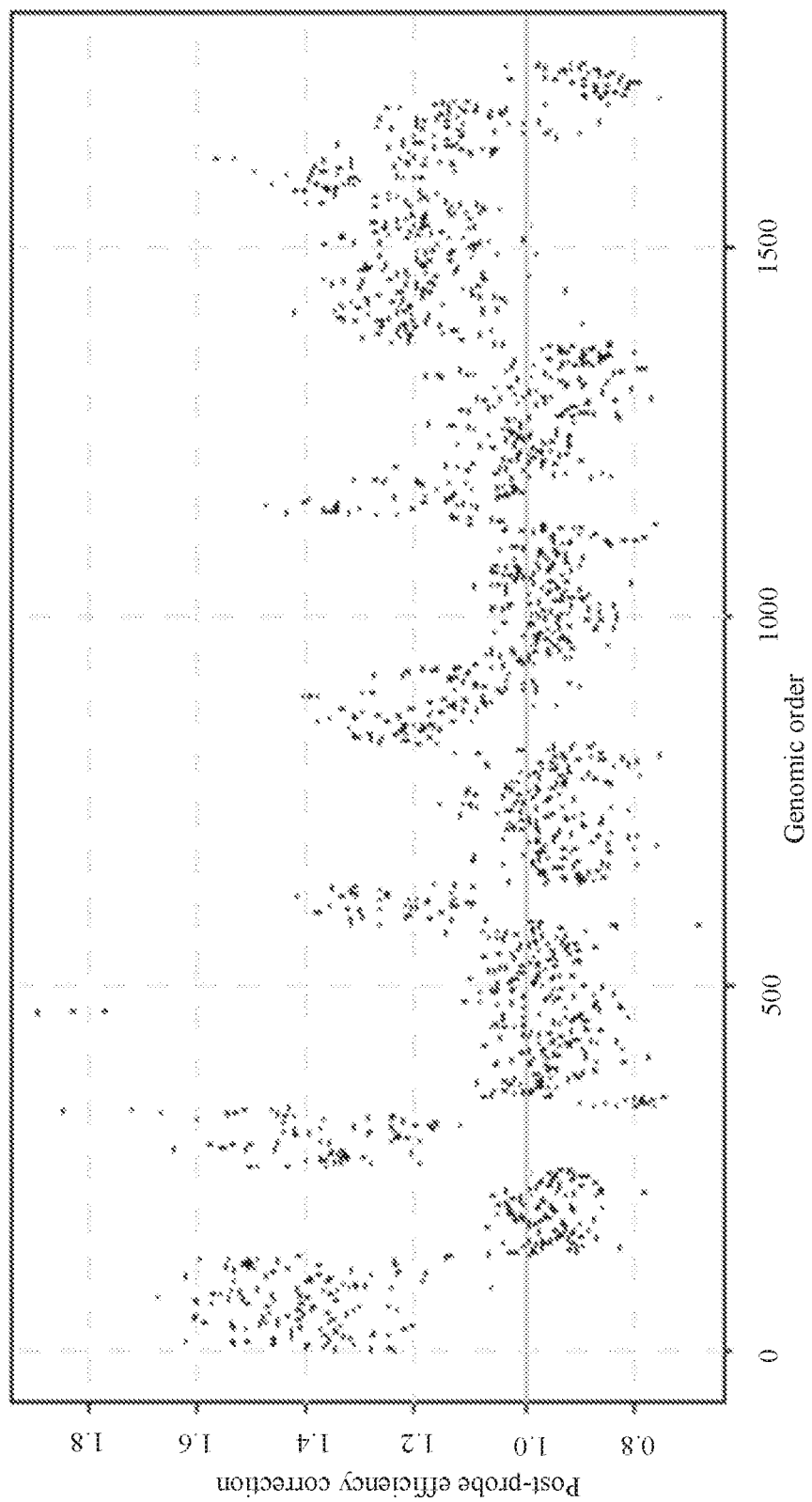
FIG. 7 illustrates post-saturation and post-probe-efficiency corrected unique molecular counts per probe.

FIG. 5 illustrates UMCs of probes without performing saturation or probe-efficiency correction. FIG. 6 shows the same sample after saturation correction. FIG. 7 shows the same sample after probe efficiency correction. The variance within genomic positions is reduced at each stage, leading to a clearer picture of the underlying copy number variation of the tumor cells emerging. Genes in FIG. 7 for which the median probe post-probe efficiency correction signal is above 1.2 are called as having undergone copy number variation. Differing levels of post-probe efficiency correction signal are likely due to tumor heterogeneity or secondary tumors.

Figure 9:
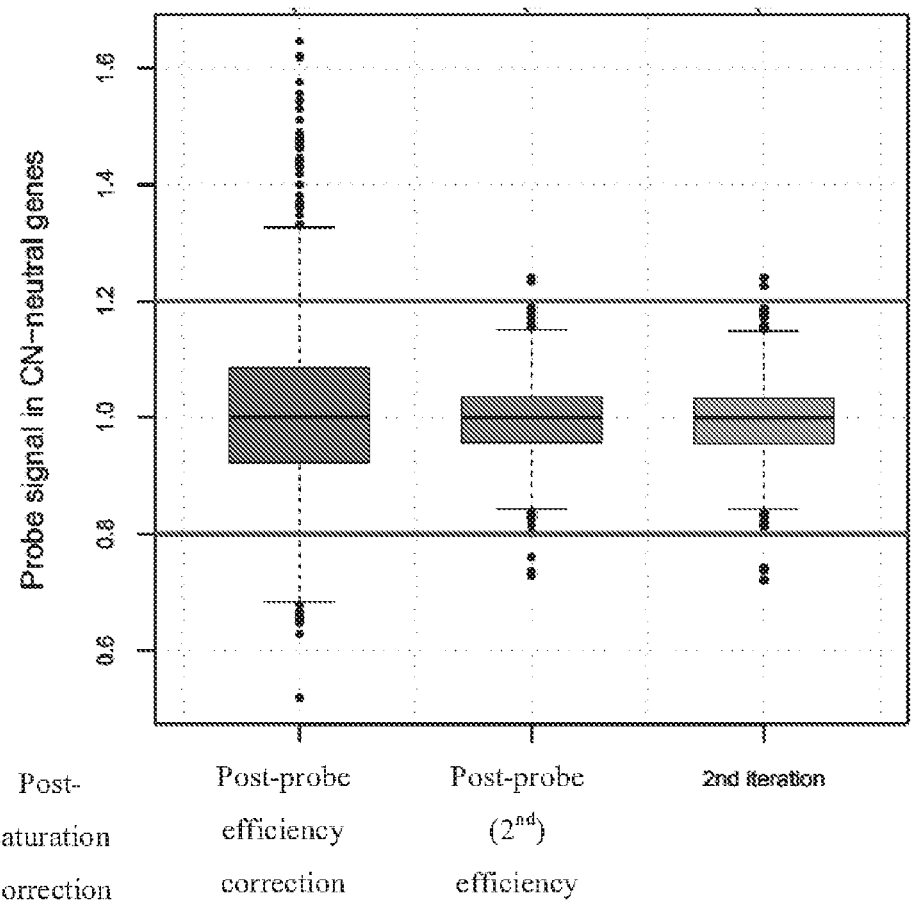
FIG. 9 illustrates the probe signal-noise reduction for the baselining genetic loci after saturation correct, probe efficiency correction, and a second round of probe efficiency correction in a typical clinical sample.

FIG. 9 shows the typical progression of baselining genetic loci probe signal noise-reduction after saturation correction and probe efficiency correction.

Figure 10A:
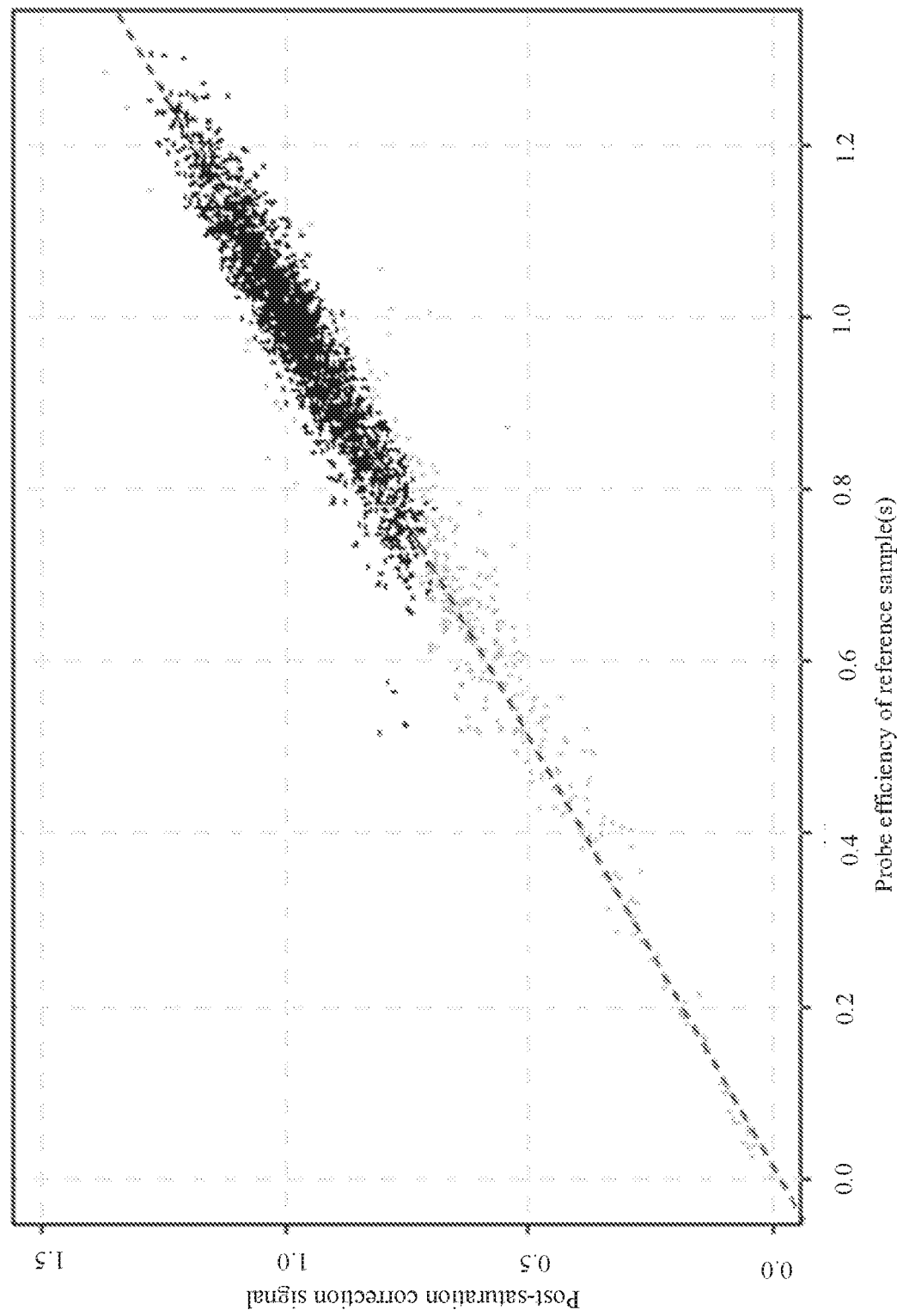
FIG. 10A and FIG. 10B illustrate post-saturation corrected UMCs plotted against the probe efficiencies determined in the reference sample in order to perform probe-efficiency correction.
Figure 10B:
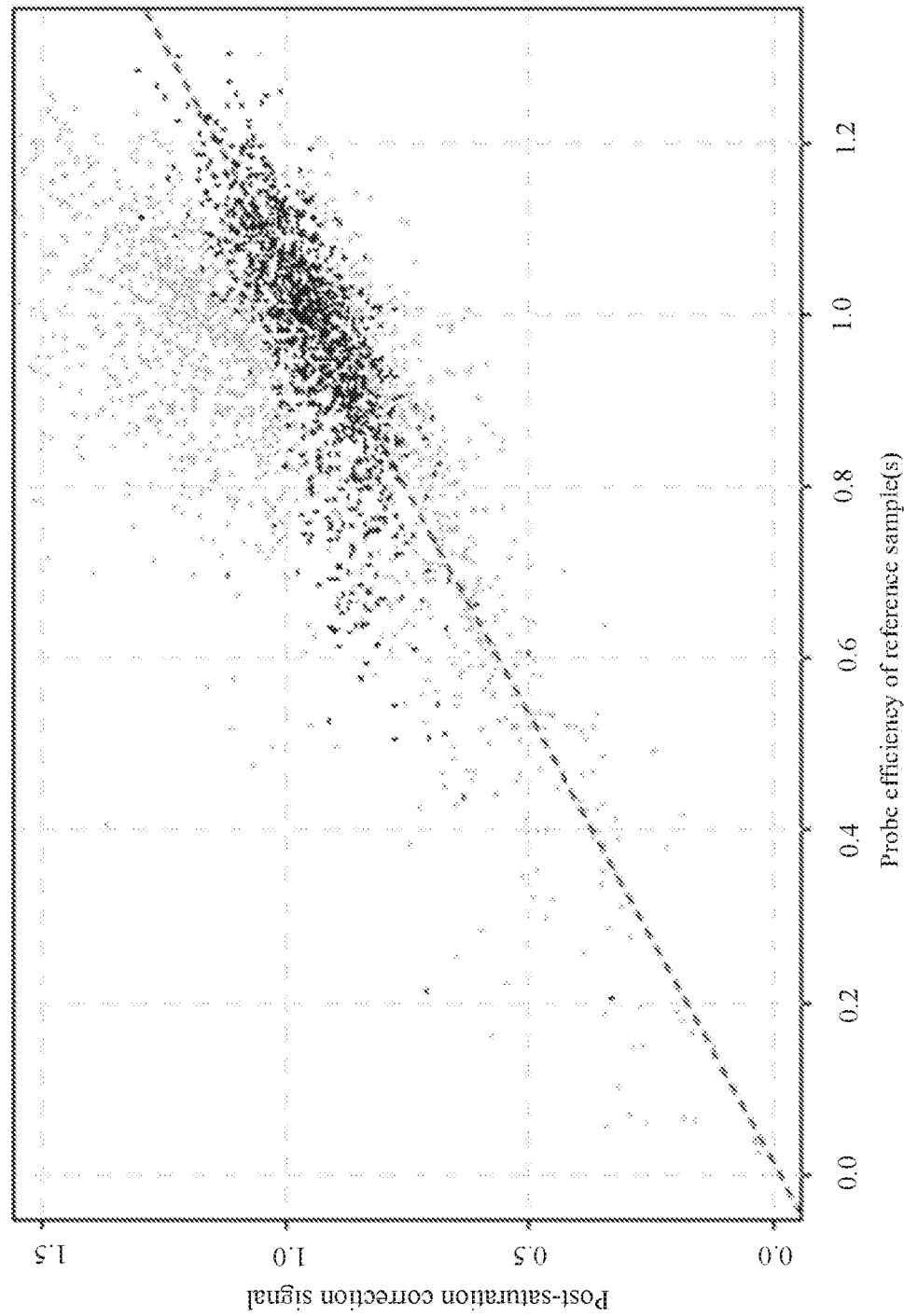
Figure 11:
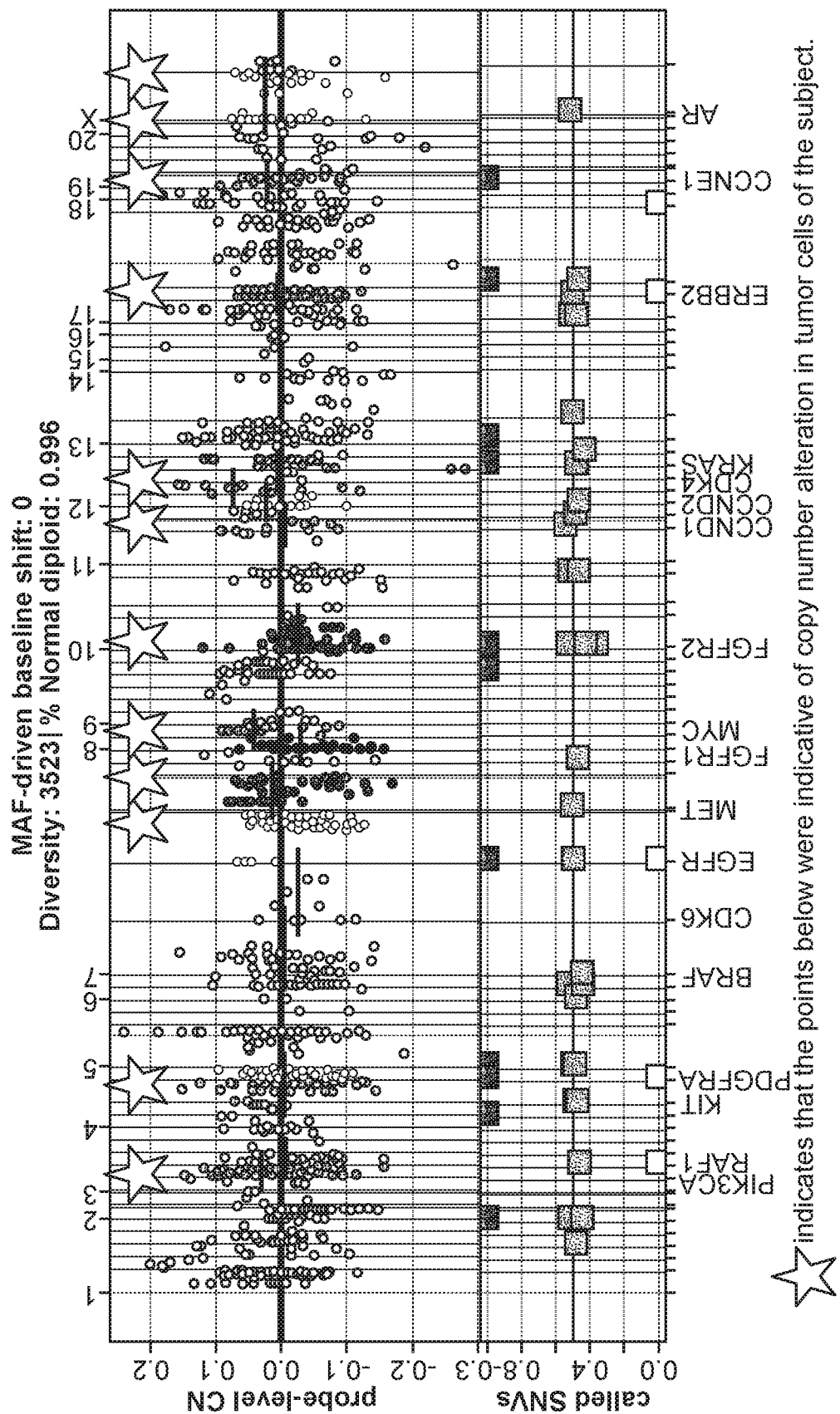
FIG. 11 illustrates a final report of saturation and probe efficiency corrected copy number variation detection in a patient sample. Stars above a sample indicate gene amplification detected based on the corrected signal and minor-allele frequency corrected baseline optimization.

FIG. 10A illustrates a plot of probe efficiency of the reference sample(s) on the x-axis and the sample's post-saturation corrected signal from a subject without copy-number variation in tumor cells. The relationship is approximately linear. FIG. 10B illustrates a similar plot from a subject with copy number variation in tumor cells. The response is not as linear as FIG. 10A. Correcting by the predicted efficiency inferred by determining the relationship between the probe efficiency from the reference sample(s) and the post-saturation corrected UMCs of the baselining genetic loci (indicated in black) will reduce variation due to differing probe efficiencies in the genetic loci that have putatively undergone copy number amplification in tumor cells (dots in grey). FIG. 11 illustrates an exemplary report of copy number variation from a patient sample based on post-saturation and probe-efficiency corrected UMCs and MAF-optimized baselining. Stars indicate points that are indicated to belong to genetic loci that have undergone copy number variation in the tumor cells of the subject.

Example 2

Cell-free DNA is obtained from a subject with cancer, a barcoded sequencing library is prepared, a panel of oncogenes is enriched by sequence capture with a probe set, and the barcoded sequencing library is sequenced. The sequencing reads are mapped to a reference genome and collapsed into families based on their barcode sequences and mapping position. For each genomic coordinate corresponding to a midpoint of a probe from the probe set, the number of read families spanning that midpoint is counted to obtain a per-probe UMC. A median per-probe UMC is determined for each gene. To perform "saturation equilibrium correction," the genes are grouped by their median per-probe GC content. Genes for which the median per-probe UMCs differs significantly from those genes with similar median per-probe GC content are removed.

For each probe, p and GC content are determined as described herein. The remaining genes from the previous step are used to perform a two-dimension second-degree polynomial surface fit of the median gene-level UMC to probe p and GC content. The function relating p and GC content to an expected UMC is used to determine expected per-probe UMCs. Residuals are determined for the data set by dividing the observed per-probe UMCs by the expected per-probe UMCs. The residual UMCs of each probe are the transformed quantitative measures of sequencing coverage.

Genes are again grouped by their median per-probe GC content, and genes whose median per-probe residual UMCs are significantly different from genes with similar median per-probe GC content are removed. "Probe efficiency" correction is then performed by obtaining residual UMCs of reference sample(s) as described in the preceding paragraphs. The residual UMCs of each probe from the sample are then divided by the residual UMCs of each corresponding probe from the reference(s) to obtain post-probe efficiency corrected UMCs.

Similar to saturation equilibrium correction above, the remaining genes are used to perform a two-dimension second-degree polynomial surface fit of the post-probe efficiency corrected UMC to probe p and GC content. The function relating p and GC content to an expected post-probe efficiency corrected UMC is used to determine an expected per-probe post-probe efficiency corrected UMC. Residuals are determined for the data set by dividing the observed per-probe post-probe efficiency corrected UMC by the expected per-probe post-probe efficiency corrected UMC. The residual post-probe efficiency corrected UMC of each probe are the post-probe GC-corrected signal.

The remaining genes are grouped by their median per-probe GC content, and genes whose median post-probe GC-corrected signal differs significantly from those genes with similar median per-probe GC content are removed.

The process of the example is repeated, with the post-probe GC-corrected signal as the starting input instead of the initial UMC.

For each gene, the median of the post-probe GC corrected signal is used to summarize each gene. Genes whose median post-probe GC-corrected signal is significantly different than the other genes are considered as candidates for having undergone gene amplification or deletion in the tumor cells.

For each gene, germline heterozygous alleles are determined and the relative frequency of each allele is quantified.

Genetic loci used for baselining are found to have an approximately 1:1 ratio of alleles, validating the selection of baselining genetic loci.

A Z-score is determined for each gene based on the gene-level median post-probe GC-corrected signals and estimated standard deviations from whole-genome normal diploid probe signals. Genes with Z-scores higher than a cut-off are reported as having undergone gene amplification in tumor cells.

Example 3

Figure 13:
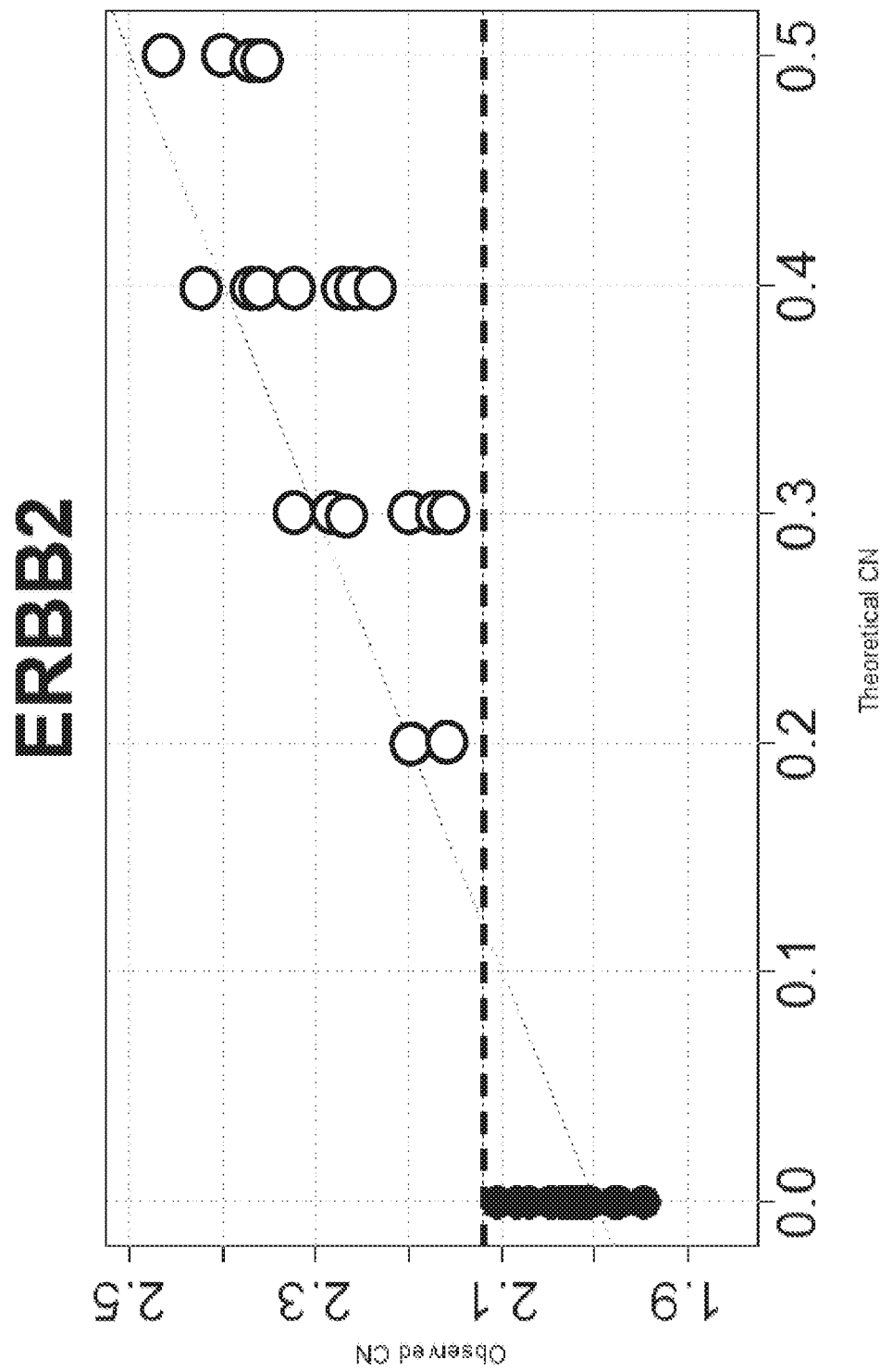
FIG. 13 illustrates observed copy number (CN) vs. theoretical CN for the gene ERBB2 as measured using a method of the present disclosure. Solid dots represent an observed copy number of ~2 (a diploid sample), open dots represent detected amplification events and the thick horizontal dashed line marks the mean gene CN cutoff.
Figure 14:
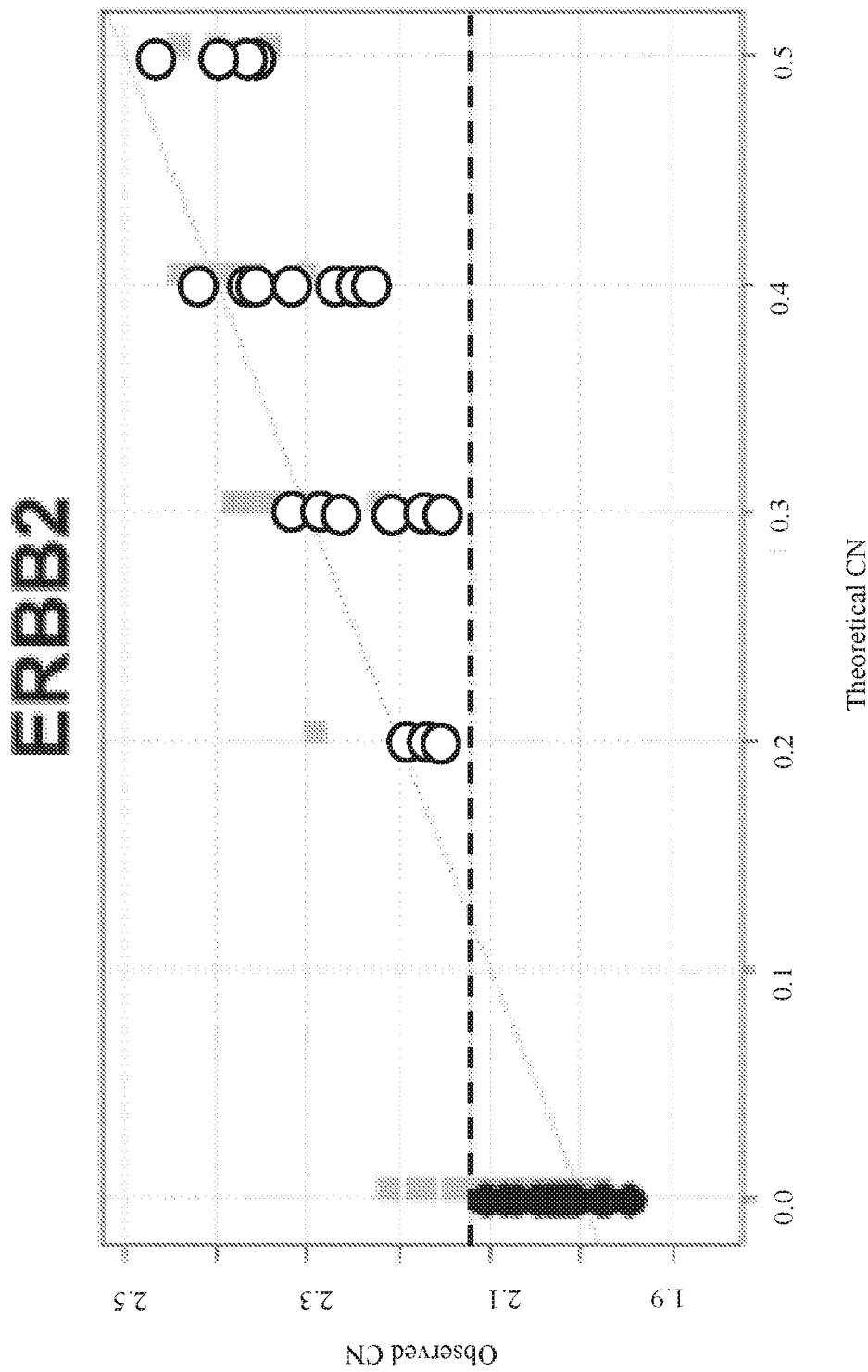
FIG. 14 illustrates observed copy number (CN) vs. theoretical CN for the gene ERBB2 as measured using a method of the present disclosure (dots) as compared to a control method (squares). Solid dots represent an observed copy number of ~2 (a diploid sample), open dots represent detected amplification events and the thick horizontal dashed line marks the mean gene CN cutoff.
Figure 15:
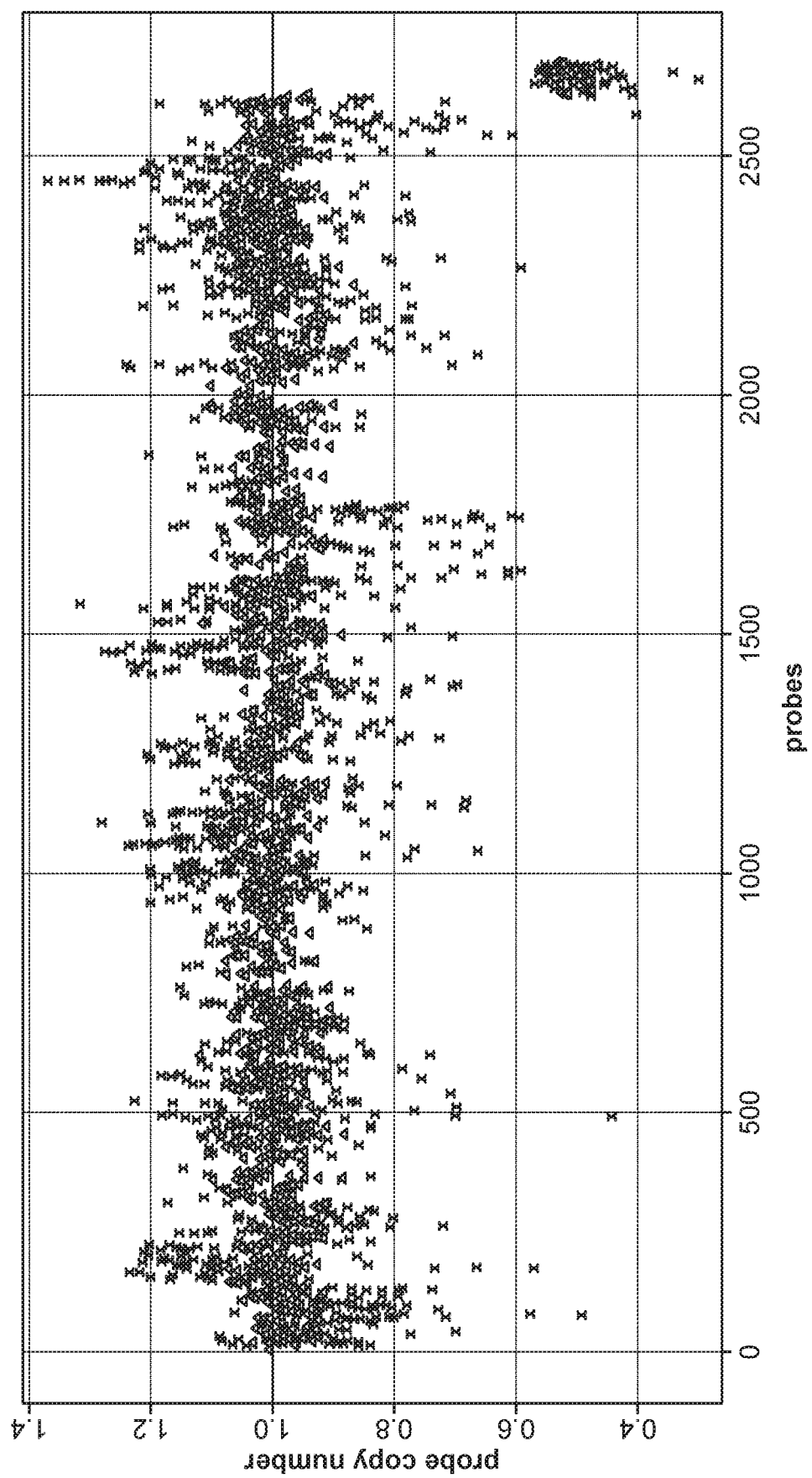
FIG. 15 illustrates probe copy number as plotted against probes used in a validation study for a method of the present disclosure (triangles) vs. a control method (X's).

The methods described herein were validated by measuring ERBB2 copy number in a method of the present disclosure against a control method. The method of the present disclosure produced a linear response of observed copy number (CN) vs. theoretical copy number, with no observed false positive CNV results in a normal (healthy) cohort. See FIG. 13, which shows the inferred gene copy number vs. the theoretical copy number estimate, with solid dots representing an observed copy number of ~2 (a diploid sample), open dots representing detected amplification events and the thick horizontal dashed line marking the mean gene CN cutoff. See also FIG. 14, which depicts the data of FIG. 13, with the control data represented by squares. All CNVs followed the expected titration trend down to 2.15 copies. Moreover, the method of the present disclosure decreased observed "noise" in the data due to a reduction in variance, allowing a CNV to be easily distinguished as compared to the control method. See the far right side of FIG. 15; triangles represent the method of the disclosure, while X's represent the control method.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for determining a copy number of one or more genetic loci, comprising a controller comprising, or capable of accessing, non-transitory computer-readable media comprising computer-executable instructions which, when executed by one or more electronic processors, perform at least:
   (a) obtaining sequencing reads of deoxyribonucleic acid (DNA) molecules of a cell-free bodily fluid sample of a subject, wherein the DNA molecules of the cell-free bodily fluid sample are enriched for a plurality of genetic loci using one or more oligonucleotide probes that are complementary to at least a portion of one or more genetic loci from the plurality of genetic loci;
   (b) generating from the sequencing reads a first data set of baselining genetic loci comprising, for one or more genetic loci of the plurality of genetic loci, a quantitative measure related to sequencing read of the one or more genetic loci;
   (c) transforming the first data set of baselining genetic loci into a saturation equilibrium-corrected data set by:
      (i) generating a quantitative measure related to guanine-cytosine (GC) content of the one or more genetic loci;
      (ii) generating a quantitative measure related to a probability that a strand of DNA molecule derived from the one or more genetic loci of the cell-free bodily fluid sample is represented within the sequence reads;
      (iii) generating a first transformation by relating the sequencing read coverage in the first data set to both the quantitative measure related to GC content of the one or more genetic loci and the quantitative measure related to a probability that a strand of DNA molecule derived from the one or more genetic loci of the cell-free bodily fluid sample is represented within the sequence reads; and
      (iv) applying the first transformation to the sequencing read coverage of the one or more genetic loci of the first data set to generate the saturation equilibrium-corrected data set, wherein the saturation equilibrium-corrected data set comprises a first set of transformed sequencing read coverages of the first data set of genetic loci;
   (d) transforming the saturation equilibrium-corrected data set into a probe efficiency-corrected data set by:
      (i) removing from the saturation-corrected data set genetic loci that are high-variance genetic loci with respect to the first set of transformed sequencing read coverages, thereby providing a second data set of baselining genetic loci;
      (ii) obtaining a second transformation that has been generated from a reference data set from sequencing reads from the one or more genetic loci of the plurality of genetic loci of one or more reference samples, wherein the second transformation has been generated by:
         (a) generating a quantitative measure related to guanine-cytosine (GC) content of the one or more genetic loci of the one or more reference samples;
         (b) generating a quantitative measure related to a probability that a strand of DNA molecule derived from the one or more genetic loci of the one or more reference samples is represented within the sequence reads of the one or more reference samples;
         (c) generating a reference transformation by relating the sequencing read coverage in the reference data set to both the quantitative measure related to guanine-cytosine (GC) content of the one or more genetic loci GC content of the one or more reference samples and the quantitative measure related to a probability that a strand of DNA molecule derived from the one or more genetic loci of the one or more reference samples is represented within the sequence reads; and
         (d) applying the reference transformation to the sequencing read coverage of the one or more genetic loci of the first data set to generate a second transformation; and (iii) applying the second transformation to the second data set of baselining genetic loci to generate the probe efficiency-corrected data set, wherein the probe efficiency-corrected data set comprises a second set of transformed sequencing read coverages of the first data set of genetic loci;

(e) obtaining a baseline sequencing read coverage for the first data set, wherein the baseline sequencing read coverage comprises an expected sequencing read coverage for the first data set based on saturation equilibrium and probe efficiency of the one or more oligonucleotide probes that are complementary to the at least the portion of the one or more genetic loci from the plurality of genetic loci; and (f) applying the baseline sequencing read coverage for the first data set to the probe efficiency-corrected data set to determine a copy number for at least one genetic locus of the one or more genetic loci relative to the baseline sequencing read coverage.

2. The system of claim 1, further comprising, prior to (c), removing genetic loci that are high-variance genetic loci from the first data set, wherein the removing comprises:

(i) fitting a model relating the quantitative measures related to GC content and the quantitative measures related to sequencing read coverage of the genetic loci; and (ii) removing from the first data set a subset of the plurality of genetic loci, wherein removing the subset comprises removing at least 10% of the plurality of genetic loci that most differ from the model, thereby providing the first data set of baselining genetic loci.

3. The system of claim 2, wherein applying the first transformation comprises (i) determining a measure related to central tendency of the sequencing read coverage of the first data set of baselining genetic loci; (ii) determining a function that fits the measure related to central tendency of the sequencing read coverage of the first data set of baselining genetic loci based on the GC content of the genetic locus and the quantitative measure related to the probability that a strand of DNA molecule of the DNA molecules derived from the genetic locus is represented within the sequencing reads; and (iii) for one or more genetic loci of the first data set of baselining genetic loci, determining a difference between a predicted sequencing read coverage determined using the function and the sequencing read coverage, thereby determining a transformed sequencing read coverage.

4. The system of claim 3, wherein the function is a surface approximation.

5. The system of claim 1, wherein removing from the saturation-corrected data set genetic loci that are high-variance genetic loci comprises:

(i) fitting a model relating the GC content and the first set of transformed sequencing read coverages of the saturation-corrected data set; and (ii) removing from the saturation-corrected data set a subset of the genetic loci, wherein removing the subset comprises removing at least 10% of the genetic loci that most differ from the model, thereby providing the second data set of baselining genetic loci.

6. The system of claim 1, wherein the GC content of one or more genetic loci of the plurality of genetic loci is a measure related to central tendency of GC content of the one or more oligonucleotide probes.

7. The system of claim 1, wherein the sequencing read coverage of the one or more genetic loci is a measure related to central tendency of the sequencing read coverage of regions of the one or more genetic loci corresponding to the one or more oligonucleotide probes.

8. The system of claim 1, wherein obtaining the sequencing reads comprises ligating adaptors to the DNA molecules of the cell-free bodily fluid sample of the subject.

9. The system of claim 8, wherein the DNA molecules comprise duplex DNA molecules, and wherein the adaptors are ligated to the duplex DNA molecules such that each adaptor of the adaptors differently tags complementary strands of the duplex DNA molecules to provide tagged strands.

10. The system of claim 8, wherein the adaptors comprise barcode sequences.

11. The system of claim 10, wherein determining the sequencing read coverage comprises collapsing the sequencing reads based at least in part on a position of the mapping of the sequencing reads to the reference genome and the barcode sequences.

12. The system of claim 1, wherein obtaining the sequencing reads comprises ligating adaptors to the DNA molecules of the cell-free bodily fluid sample of the subject, wherein the DNA molecules comprise duplex DNA molecules, wherein the adaptors are ligated to the duplex DNA molecules such that each adaptor of the adaptors differently tags complementary strands of the duplex DNA molecules to provide tagged strands, and wherein determining the quantitative measure related to the probability that a strand of DNA derived from the genetic locus is represented within the sequencing reads comprises sorting the sequencing reads into paired reads and unpaired reads, wherein (i) each paired read of the paired reads corresponds to sequencing reads generated from a first tagged strand and a second differently tagged complementary strand derived from a double-stranded DNA molecule of the DNA molecules, and (ii) each unpaired read of the unpaired reads represents a first tagged strand having no second differently tagged complementary strand derived from a double-stranded DNA molecule represented among said sequencing reads of the sequencing reads.

13. The system of claim 12, wherein quantitative measures of (i) the paired reads and (ii) the unpaired reads that map to each of one or more genetic loci are determined, to produce a quantitative measure related to total double-stranded DNA molecules of the cell-free bodily fluid sample that map to each of the one or more genetic loci based on the quantitative measures of the paired reads and the unpaired reads mapping to each genetic locus of the one or more genetic loci.

14. The system of claim 1, wherein the computer-executable instructions, when executed by the one or more electronic processors, further determine that at least a subset of the baselining genetic loci have undergone copy number alteration in tumor cells of the subject by determining relative quantities of variants within the baselining genetic loci for which a germline genome of the subject is heterozygous.

15. The system of claim 14, wherein the relative quantities of the variants are not approximately equal, and wherein the computer-executable instructions, when executed by the one or more electronic processors, further remove genetic loci from the baselining genetic loci for which the relative quantities of the variants are not approximately equal, thereby providing allelic frequency-corrected baselining genetic loci.

16. The system of claim 1, wherein the one or more reference samples comprise DNA molecules of a cell-free bodily fluid sample of a subject without cancer.

17. The system of claim 1, wherein the one or more reference samples comprise DNA molecules of a cell-free bodily fluid sample of a subject with cancer, wherein the at least one genetic locus determined in (e) has not undergone copy number alteration in the one or more reference samples.

18. The system of claim 1, wherein the plurality of genetic loci comprises a midpoint of the one or more oligonucleotide probes, and wherein the quantitative measure related to the sequencing read comprises unique molecule counts at one or more genetic loci of the plurality of genetic loci.

* * * * *